US006846670B2

(12) United States Patent
Schwartz et al.

(10) Patent No.: US 6,846,670 B2
(45) Date of Patent: Jan. 25, 2005

(54) GENETICALLY ENGINEERED HERPES VIRUS FOR THE TREATMENT OF CARDIOVASCULAR DISEASE

(75) Inventors: Lewis B. Schwartz, Hinsdale, IL (US); Ralph R. Weichselbaum, Chicago, IL (US); Bernard Roizman, Chicago, IL (US)

(73) Assignee: The University of Chicago, Chicago, IL (US)

( * ) Notice: Subject to any disclaimer, the term of this patent is extended or adjusted under 35 U.S.C. 154(b) by 27 days.

(21) Appl. No.: 09/995,475

(22) Filed: Nov. 28, 2001

(65) Prior Publication Data

US 2002/0155432 A1 Oct. 24, 2002

Related U.S. Application Data

(60) Provisional application No. 60/253,680, filed on Nov. 28, 2000.

(51) Int. Cl.[7] ............................................... C12N 15/00
(52) U.S. Cl. ................ 435/320.1; 435/69.1; 435/235.1; 424/229.1; 424/199.1
(58) Field of Search .......................... 435/320.1, 235.1, 435/234, 325, 236, 69.1; 424/229.1, 231.1, 199.1; 536/23.72

(56) References Cited

U.S. PATENT DOCUMENTS

| | | | |
|---|---|---|---|
| 4,859,587 A | 8/1989 | Roizman | 435/68 |
| 5,288,641 A | 2/1994 | Roizman | 435/320.1 |
| 5,328,688 A | 7/1994 | Roizman | 424/205.1 |
| 5,585,096 A | 12/1996 | Martuza et al. | 424/93.2 |
| 5,599,691 A | 2/1997 | Roizman | 435/69.1 |
| 5,641,651 A | 6/1997 | Roizman | 435/69.1 |
| 5,728,379 A | 3/1998 | Martuza et al. | 424/93.2 |
| 5,795,713 A | 8/1998 | Roizman | 435/5 |
| 5,824,318 A | 10/1998 | Mohr et al. | 424/229.1 |
| 5,837,262 A | 11/1998 | Golubev et al. | 424/231.1 |
| 5,846,707 A | 12/1998 | Roizman | 435/5 |
| 5,851,826 A | 12/1998 | Fraefel et al. | 435/325 |
| 5,879,934 A | 3/1999 | DeLuca | 435/320.1 |
| 6,071,692 A | 6/2000 | Roizman | 435/5 |
| 6,106,826 A | 8/2000 | Brandt et al. | 424/93.2 |
| 6,120,773 A | 9/2000 | Roizman | 424/205.1 |

FOREIGN PATENT DOCUMENTS

| WO | WO 98/04726 | * | 2/1998 |
| WO | WO 98/42195 | * | 10/1998 |

OTHER PUBLICATIONS

Detrait et al, Molecular Therapy, 2002, vol. 5, No. 6, pp. 723–730.*
Smith AE (The Lancet, 1999, vol. 354 suppl. 1, pp 1–4.*
Verma et al, Nature, 1997, vol. 389, pp. 239–242.*
Coffin, et al. "Gene Delivery to the Heart In Vivo and to Cardiac Myocytes and Vascular Smooth Muscle Cells In Vitro Using Herpes Virus Vectors," *Gene Therapy* 3:560–566 (1996).
Mesri, et al., "Expression of Vascular Endothelial Growth Factor From a Defective Herpes Simplex Virus Type 1 Amplicon Vector Induces Angiogenesis in Mice," *Circulation Research* 76:161–167 (1995).
Robbins et al., "Viral Vectors for Gene Therapy," *Pharmacol. Ther.* 80 (1):35–47 (1998).
Yeh, et al., "Advances in Adenoviral Vectors: From Genetic Engineering to Their Biology," *FASEB Journal* 11 (8):615–623 (1997).
International Search Report, PCT/US01/44279, Nov. 26, 2002.
Advani et al., "Enhancement of replication of genetically engineered herpes simplex viruses by ionizing radiation: a new paradigm for destruction of therapeutically intractable tumors," *Gene Ther*, 5:160–165, 1998.
Alber et al., "Herpesvirus infection accelerates atherosclerosis in the apolipoprotein E–deficient mouse," *Circ*, 102:779–785, 2000.
Andreansky et al., "Evaluation of genetically engineered herpes simplex viruses as oncolytic agents for human malignant brain tumors," *Can Res*, 57:1502–1509, 1997.
Baumgartner et al., "Constitutive expression of ph VEGF165 after intramuscular gene transfer promotes collateral vessel development in patients with critical limb ischemia," *Circ*, 97:1114–1123, 1998.
Chambers et al., "Comparison of genetically engineered herpes simplex virus for the treatment of brain tumors in SCID mouse model of human glioma," *PNAS*, 92:1411–1415, 1995.
Chandler et al., "RNA splicing specificity determined by the coordinated action of RNA recognition motifs in SR proteins," *Proc Natl Acad Sci U S A.*, 94(8):3596–3601, 1997.
Chou and Roizman, "Herpes simplex virus 1 gamma–1 34.5 gene function, which blocks the host response to infection, maps in the homologous domain of the genes expressed during growth arrest and DNA damage," *Proc Natl Acad Sci*, 91:5247–5251, 1994.
Chou et al., "Mapping of herpes simplex virus–1 neurovirulence to gamma$_1$34.5, a gene nonessential for growth in culture," *Science*, 250:1262–1266, 1990.

(List continued on next page.)

*Primary Examiner*—Ali R. Salimi
(74) *Attorney, Agent, or Firm*—Marshall, Gerstein & Borun LLP

(57) ABSTRACT

The present invention provides methods of expressing a nucleic acid or producing a proteinaceous composition encoded by a nucleic acid in vascular and cardiovascular cells by administration of a herpesvirus vector. The present invention provides methods of producing a therapeutic benefit in vascular and cardiovascular tissue by administration of a herpesvirus vector. In additional aspects, the invention concerns combination therapies for vascular and cardiovascular diseases comprising administration of a herpesvirus vector and treatment with at least one addition pharmacological agent or surgical procedure.

28 Claims, No Drawings

OTHER PUBLICATIONS

Dollery et al., "Expression of tissue inhibitor of matrix metalloproteinases 1 by use of an adenoviral vector inhibits smooth muscle cell migration and reduces neointima hyperplasia in the rat model of vascular balloon injury," *Circ*, 99:3199–3205, 1999.

George et al., "Inhibition of late vein graft neointima formation in human and porcine models by adenovirus–mediated overexpression of tissue inhibitor of metalloproteinase–3," *Circ*, 101:296–304, 2000.

Hanna et al., "Adenoviral–mediated expression of antisense RNA to basic fibroblast growth factor reduces tangential stress in arterialized vein grafts," *J Vasc Surg*, 31:770–780, 2000.

Huard, Goins, Fink, "Herpes simplex virus type I vector mediated gene transfer to muscle," Gene Ther, 2:385–392, 1995.

Isner et al., "Arterial gene therapy for therapeutic angiogenesis in patients with peripheral artery disease," *Circ*, 91:2687–2692, 1995.

Key et al., "Infection of vascular endothelial cells with herpes simplex virus enhances tissue factor activity and reduces thrombomodulin expression," *Proc Natl Acad Sci*, 87:7095–7099, 1990.

Lachmann et al., "The use of herpes simplex virus–based vectors for gene delivery to the nervous system," *Molec Med Today*, 3:404–411, 1997.

Martuza et al., "Experimental therapy of human glioma by means of a genetically engineered virus mutant," *Science*, 252:854–856, 1991.

Meyerson et al., "The effects of extremely low shear stress on cellular proliferation and neointimal thickening in the failing bypass graft," *J. Vasc. Surg.*, 34:90–97 (2001).

Mineta, Rabkin, Martuza, "Treatment of malignant gliomas using ganciclovir–hypersensitive, ribonucleotide reductase–deficient herpes simplex viral mutant," *Cancer Res*, 54:3963–3966, 1994.

Miyatake et al., "Inhibition of rat vascular smooth muscle cell proliferation in vitro and in vivo by recombinant replication–competent herpes simplex virus," *Stroke*, 30:2431–2438, 1999.

Moawad et al., "Adenoviral–mediated gene transfer in human and animal vein grafts using clinically relevant exposure times, pressures, and viral concentrations," *Ann. Vasc. Surg.*, 15:367–373 (2001).

Nabel et al., "Recombinant fibroblast growth factor–1 promotes intimal hyperplasia and angiogenesis in arteries in vivo," *Nature*, 362:844–846, 1993.

Nicolau et al., "Liposomes as carriers for in vivo gene transfer and expression," *Methods Enzymol.*, 149:157–176, 1987.

Roizman, B., "The function of herpes simplex virus genes: A primer for genetic engineering of novel vectors," *Proc. Natl. Acad. Sci.*, 93:11307–11312 (1996).

Rosengart et al., "Angiogenesis gene therapy: phase I assessment of direct intramyocardial administration of an adenovirus vector expressing VEGF121 cDNA to individuals with clinically significant severe coronary artery disease," *Circ*, 100:468–474, 1999.

Scheinman, et al., "p53 gene transfer to the injured rat carotid artery decreases neointimal formation," *J Vasc Surg*, 29:360–369, 1999.

Schneider et al., "Adventitial delivery minimizes the proinflammatory effects of adenoviral vectors," *J Vasc Surg*, 29:543–550, 1999.

Schwartz and Moawad, "Gene therapy for vascular disease," *Ann Vasc Surg*, 11:189–99, 1997.

Schwartz et al., "Adenoviral–mediated transfer of a constitutively active formof the retinoblastoma gene product attenuates neointimal thickening in experimental vein grafts," *J Vasc Surg*, 29:874–883, 1999.

Svensson et al., "Efficient and stable transduction of cardiomyocytes after intramyocardial injection or intracoronary perfusion with recombinant adeno–associated virus vectors," *Circ*, 99:201–205, 1999.

Symes et al., "Gene therapy with vascular endothelial growth factor for inoperable coronary artery disease," *Ann Thor Surg*, 68:830–836, 1999.

Treisman, "Transient Accumulation of c–fos RNA Following Serum Stimulation Requires a Conserved 5' Element and c–fos 3' Sequences," *Cell*, 42:889, 1985.

Waugh et al., "Thrombomodulin overexpression to limit neointima formation," *Circ*, 102:332–337, 2000.

* cited by examiner

GENETICALLY ENGINEERED HERPES VIRUS FOR THE TREATMENT OF CARDIOVASCULAR DISEASE

Priority is claimed to U.S. Provisional Patent Application No. 60/253,680, filed Nov. 28, 2000.

The United States Government may own certain rights in this invention.

BACKGROUND OF THE INVENTION

1. Field of the Invention

The present invention relates generally to the fields of genetic therapy. More particularly, it concerns administration of a herpes simplex viral vector to produce a therapeutic benefit in vascular and cardiovascular tissue. In additional aspects, the invention concerns combination therapies comprising administration of a herpes simplex viral vector and treatment with at least one additional pharmacological agent or surgical procedure, as well as use of surgical procedures and other targeting means to facilitate delivery of the herpes simplex virus vectors to vascular cells and tissues.

2. Related Technology

Vascular disease remains the leading cause of death and disability in the Western world [McGovern et al., *New Engl. J. Med.* 334:884–890, 1996]. Current treatment strategies are primarily aimed at risk factor modification and/or mechanical remediation of critical lesions. Although these strategies are often effective, the ability to genetically alter the basic pathophysiologic defects within diseased vascular tissue would offer a new paradigm of therapy and possibly revolutionize the treatment of vascular disease. The feasibility of vascular gene transfer was first demonstrated in 1989 when it was shown endothelial cells (EC's) expressing the retrovirally transduced lacZ gene could adhere and function in porcine iliac arteries [Nabel et al., *Science* 244:1342–1344, 1989]. Since then, nearly one billion U.S. dollars annually have been spent to refine and improve systems of transfer vectors and delivery systems [Svensson et al., *Curr. Opin. Cardio.* 13:369–374, 1998].

A variety of vectors have been used to transfer genes to vascular tissue, with variable results. Each of the most popular vector systems—naked plasmid DNA (Isner et al., *Hum. Gene Ther.* 7:989–1011, 1996; Baumgartner et al., *Circ.* 97:1114–1123, 1998], liposome-encapsulated DNA, [Armeanu et al., *Mol. Ther.* 1:366–375, 2000] retrovirus [Geary et al., *Hum. Gene Ther.* 5:1211–1216, 1994], adeno-associated virus (AAV) [Lynch et al., *Circ. Res.* 80:497–505, 1997], and adenovirus [Kay, *J. Vasc. Surg.* 24:160–161, 1996; Yeh et al., *FASEB J.* 11:615–623, 1997], have met with some success depending on the application. Efforts at gene transfer using only naked plasmid DNA have met with limited success due to low transfection efficiency [Baumgartner et al., *Circ.* 97:1114–1123, 1998; Reissen et al., *Hum. Gene Ther.* 4:449–458, 1993; Turunen et al., *Gene Ther.* 6:6–11, 1999]. DNA encapsulated within liposomes is somewhat more efficient [Armeanu et al., *Mol. Ther.* 1:366–375, 2000; Turunen et al., *Gene Ther.* 6:6–11, 1999; Takeshita et al., *J. Clin. Invest.* 93:652–661, 1994; Lim et al., *Circ.* 83:2007–2011, 1991; Matsumoto et al., *J. Vasc. Surg.* 27:135–144, 1998; Matsumura et al., *J. Surg. Res.* 85:339–345, 1999] but generally lacks complete penetrance with an intact basement membrane. Retrovirus was tested in early experiments [Nabel et al., *Science* 244:1342–1344, 1989; Dunn et al., *Circ.* 99:3199–3205, 1996], as well as more recently to transfer antisense oligonucleotides [Zhu et al., *Circ.* 96:628–635, 1997], but suffers greatly from its low efficiency in non-dividing cells. A relatively new vector system, adeno-associated virus (AAV), has been shown to efficiently infect skeletal muscle without inciting an intense immune response [Muzyczka, *Curr. Topics Microbiol. Immunol.* 158:97–129, 1992], and preliminary results have demonstrated that AAV is capable of transfecting vascular EC's [Lynch et al., *Circ. Res.* 80:497–505, 1997; Rolling et al., *Gene Ther.* 4:757–761, 1997; Kotin, *Hum. Gene. Ther.* 5:793–801, 1994; Xiao et al., *J. Virol.* 70:8098–8108, 1996] smooth muscle cells (SMC's, Rolling et al., *Gene Ther.* 4:757–761, 1997), and cardiocytes [Svensson et al., *Circ.* 99:201–205, 1999]. A recent report, however, indicates that gene transfer into vascular tissue with an intact endothelium may be problematic, with only 1–14% of cells staining positive after 30 days [Eslami et al., *J. Vasc. Surg.* 31:1149–1159, 2000].

Certainly, the most widely tested vector for vascular gene transfer has been replication-deficient adenovirus [Yeh et al., *FASEB J.* 11:615–623, 1997]. Adenoviral vectors exhibit a high penetrance in non-dividing cells, can be produced in high concentration, and can house relatively large transgenes. They have been used experimentally in vascular tissue to transfer a wide variety of marker and biologically active genes including Rb, [Chang et al., *J. Clin. Invest.* 95:2260–2268, 1995; Smith et al., *Circ.* 96:1899–1905, 1997] p21, [Chang et al., *J. Clin. Invest.* 95:2260–2268, 1995; Scheinman et al., *J. Vasc. Surg.* 29:360–369, 1999] cytosine deaminase [Harrell et al., 1997; Fortunato et al., 2000), C-type natriuretic peptide (Ueno et al., 1997), metalloproteinase inhibitors (Cheng et al., 1998; George et al., 2000; Dollery et al., 1999), hirudin, (Bishop et al., 1999) cyclooxygenase (Zoldhelyi et al., 1996), tissue factor pathway inhibitor (Zoldhelyi et al., 2000), thrombomodulin (Waugh et al., 2000), ecNOS (Varenne et al., 1998; Cable et al., 1999), βARKCT, (Fulton et al., 1996) and antisense RNA to bFGF (Hanna et al., 1997; Neschis et al., 1998; Hanna et al., 2000). The success of many of these protocols has been due, in part, to the very high concentration of vector used, as well as use of the popular model of creating injury by balloon inflation, which denudes endothelium and enhances vector penetration.

Gene transfer into intact vascular tissue, such as non-injured arteries or vein grafts, has proved more difficult (Eslami et al., 2000; Schwartz et al., 1999; Fulton et al., 1996; Hanna et al., 2000; Mann et al., 1995; Fulton et al., 1997; Fulton et al., 1998; Faries et al., 2000). Transfer efficiency is generally lower, the required doses are high, and the biologic effects less pronounced (Schwartz et al., 1999; Fulton et al., 1996; Hanna et al., 2000; Mann et al., 1995; Fulton et al., 1997; Fulton et al., 1998; Faires et al., 2000). Furthermore, and perhaps most importantly, an intact immune system remains a serious impediment to long-term transgene expression using adenovirus, as neutralization of the cytosolic episome generally is complete after the first week (Eslami et al., 2000; Chang et al., 1995). Immunomodulation of the host can extend the life of the transgene [Ascher et al., *Ann. Vasc. Surg.* 14:385–392, 2000], but global immunosuppression in the elderly population with vascular disease is clearly impractical. The problems inherent in adenoviral-based gene transfer in vascular tissue is best illustrated by the fact that, to date, only a single trial of therapeutic gene transfer has been reported [for angiogenesis, Rosengart et al., 1999], and there has yet to be a published clinical trial using adenoviral vectors for the treatment or prevention of vascular proliferative disorders.

A potential vector for the generation of long-term transgene expression is herpes simplex virus type one (HSV-1).

HSV-1 is the virus that is responsible for recurrent oropharyngeal cold sores. It is a lytic, nonintegrating DNA virus that has demonstrated neurotropism and the establishment of long-term infections. Like adenovirus, HSV-1 can be manufactured in high titer and contains multiple non-essential genes that can potentially be deleted and replaced with large transgenes. This had led to speculation that the use of HSV may become a method for gene transfer for systemic disease (Culver, 1996; Lachmann and Efstathiou, 1997). However, the lytic and highly infectious nature of HSV, and the lifelong potential for latency, necessitate significant genetic modification prior to therapeutic use (Lachmann and Efstathiou, 1997; Huard et al., 1995; Advani et al., *Gene Therapy* 5:160–165, 1998]. The first set of recombinant herpesviruses to be generated lacked one or more genes (e.g., thymidine kinase or ribonucleotide reductase), which only moderately reduced viral growth in non-dividing cells (Martuza et al., 1991; Mineta et al., 1994; Miyatake et al., 1999). HSV-1 has been extensively studied as therapy for malignant tumors of the central nervous system using a variety of genetic manipulations [Advani et al., *Gene Therapy* 5:160–165, 1998; Chambers et al., 1995; Andreansky et al., *Can. Res.* 57:1502–1509, 1997]. More recently, attempts to render the virus nonvirulent have been made through deletion of both copies of the $\gamma_1 34.5$ gene (Chou et al., 1990; Chou and Roizman, 1994).

However, the inventors are only aware of two phase I clinical trials using transfer vectors and delivery systems, both addressing the feasibility of transfer of angiogenic factors [Baumgartner et al., *Circ.* 1114–1123, 1998; Isner et al., 1995; Symes et al., 1999; Rosengart et al., 1999). Thus, despite the advances in the art, there is still a need for more effective vectors and methods of therapy for a wider application of somatic gene therapy to treat vascular disease.

SUMMARY OF THE INVENTION

The present invention provides a solution to the aforementioned problem by providing a method of expressing a heterologous nucleic acid in a vascular cell via the use of a recombinant herpes simplex virus. The present invention also provides a method of treating or preventing vascular disease as well as a method directed to inducing normal physiology in a functionally abnormal vascular According to one aspect of the invention a method of expressing a heterologous nucleic acid sequence in a vascular cell is provided. The method comprises administering to the vascular cell a recombinant replicating herpes simplex viral vector, wherein the herpes simplex virus comprises a heterologous nucleic acid, and wherein the herpes simplex virus is debilitated for growth in the central nervous system.

The recombinant herpes simplex virus is debilitated for growth via non-silent insertion, substitution, or deletion of a nucleotide sequence in at least one non-essential gene of the herpes simplex virus. In a related embodiment, the recombinant herpes simplex virus may further comprise a non-silent insertion, substitution, or deletion of a nucleotide sequence in at least one essential gene of the herpes simplex virus. In one embodiment, the herpes simplex virus lacks one expressible $\gamma_1 34.5$ gene, a non-essential gene. In a further embodiment, the recombinant herpes simplex lacks both expressible $\gamma_1 34.5$ genes.

Suitable vascular cells for treatment by the present method would include an endothelial cell, a smooth muscle cell, and/or an adventitial cell. In a further embodiment the heterologous nucleic acid sequence encodes a polypeptide, i.e., an antiproliferative polypeptide, a vasodilatory polypeptide, and an angiogenic polypeptide. In an additional embodiment the heterologous nucleic acid sequence encodes an antisense oligonucleotide or antisense polynucleotide. In a further embodiment, the antisense oligonucleotide or antisense polynucleotide is complementary to an RNA encoding an antiproliferative polypeptide, vasodilatory polypeptide, or angiogenic polypeptide. Preferably, the recombinant herpes simplex virus is HSV-1. In a related embodiment, the recombinant herpes simplex virus further comprises at least one gene essential for the treatment of a herpes simplex virus infection by an anti-viral agent.

According to another aspect of the present invention, a method is provided for treating or preventing a cardiovascular disease or condition in a vascular cell comprising administering to the cell a recombinant replicating herpes simplex viral vector comprising a heterologous nucleic acid sequence, and wherein the herpes simplex virus is debilitated for growth in the central nervous system.

The recombinant herpes simplex virus is debilitated for growth via non-silent insertion, substitution, or deletion of a nucleotide sequence in at least one non-essential gene of the herpes simplex virus. The recombinant herpes simplex virus may further comprise a non-silent insertion, substitution, or deletion of a nucleotide sequence in at least one essential gene of the herpes simplex virus. In one embodiment, the herpes simplex virus lacks one expressible $\gamma_1 34.5$ gene, a non-essential gene. In a further embodiment, the recombinant herpes simplex lacks both expressible $\gamma_1 34.5$ genes.

In a preferred embodiment the cardiovascular condition is hypertension in a vascular tissue. Preferably, the cardiovascular condition is selected from the group consisting of chronic heart failure, hypertensive cardiovascular disease, ischemic heart disease, arrhythmia, congenital heart disease, valvular heart disease or stenotic defect, cardiomyopathy, aneurysm, chronic venous insufficiency, peripheral arterial disease, or restenosis.

In an additional embodiment, the heterologous nucleic acid sequence is expressed in vascular tissue for a duration selected from the group consisting of more than 7 days, more than 14 days, more than 21 days, more than 28 days, more than 35 days, or more than 70 days.

A further embodiment calls for the heterologous nucleic acid sequence to encode a screenable or selectable marker. Preferably, the heterologous nucleic acid sequence is an antithrombotic nucleic acid, an angiogenesis regulating nucleic acid, an immunomodulator, an inducer of cellular proliferation, an inhibitor of cellular proliferation or a regulator of programmed cell death.

In a related embodiment, the method of the present invention further comprises administering at least one therapeutic or pharmacological agent to the vascular cell. In a preferred embodiment, the pharmacological agent is selected from the group consisting of an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, and an anti-infection agent. Preferably, the recombinant herpes simplex virus is HSV-1. In a related embodiment, the recombinant herpes simplex virus further comprises at least one gene essential for the treatment of a herpes simplex virus infection by an anti-viral agent.

In yet another aspect of the present invention a method is provided for inducing normal physiology in a functionally abnormal vascular cell comprising administering to the cell a recombinant replicating herpes simplex viral vector comprising a heterologous nucleic acid sequence, and wherein the herpes simplex virus is debilitated for growth in the central nervous system.

The recombinant herpes simplex virus is debilitated for growth via non-silent insertion, substitution, or deletion of a nucleotide sequence in at least one non-essential gene of the herpes simplex virus. The recombinant herpes simplex virus may further comprise a non-silent insertion, substitution, or deletion of a nucleotide sequence in at least one essential gene of the herpes simplex virus.

Other features and advantages of the present invention will be better understood by reference to the detailed description and examples that follow.

DETAILED DESCRIPTION OF THE INVENTION

Somatic gene transfer has been proposed as a method to treat a variety of ischemic, thrombotic, and proliferative vascular disorders. However, progress in the field of vascular gene transfer has been hampered by a lack of vectors that can effectively penetrate the endothelium and stably and durably transform, transfect, or infect deeper cell layers.

Recently, the neurovirulence of herpes simplex virus type one (HSV-1) has been genetically attenuated, resulting in significantly reduced toxicity, while still maintaining its ability to penetrate and establish long-term infections. Deletion of both copies of the $\gamma_1 34.5$ gene potentially decreases virulence, but still allows for replication in dividing cells and, possibly, stable episomal infection. The product of the $\gamma_1 34.5$ gene blocks phosphorylation of the a subunit of the translation initiation factor eIF-2 involved in viral protein synthesis.

To overcome the deficiencies in the art, a modified recombinant form of HSV-1 wherein both copies of the $\gamma_1 34.5$ gene were deleted (Chou et al., 1990; Chou and Roizman, 1994) was evaluated for its reliability and efficiency in transfecting vascular tissue in vitro and in vivo. The HSV-1 vector and methods of use are shown herein to be highly effective for gene transfer into vascular cells, with transfection efficiency and duration far exceeding that of traditional viral vectors. The disclosures herein demonstrate that a $\gamma_1 34.5$-deleted HSV-1 vector was capable of maintaining transgene expression in 50% of arterialized venous neointima for up to four weeks in animals with an intact immune system. These results were both surprising and unexpected, as the duration and efficiency demonstrated herein far exceeds the reported results with other vectors (Eslami et al., 2000; Schwartz et al., 1999; Scheinman et al., 1999; George et al., 2000; Dollery et al., 1999; Waugh et al., 2000; Hanna et al., 2000; Schneider et al., 1999). Further surprising and unexpected properties of the vector and methods of the present invention were demonstrated by the low dose of HSV-1 required to achieve these effects. Only $10^8$ plaque forming units (pfu) per ml were used to achieve this duration and efficiency, which is a dose several orders of magnitude less than traditional strategies using adenovirus (Chang et al., 1995; Smith et al., 1997; Schwartz et al., 1999; Chang et al., 1995; Scheinman et al., 1999; Ueno et al., 1997; Cheng et al., 1998; George et al., 2000; Dollery et al., 1999; Bishop et al., 1999; Zoldhelyi et al., 2000; Waugh et al., 2000; Varenne et al., 1998; Cable et al., 1999; Fulton et al., 1996; Hanna et al., 1997; Neschis et al., 1998; Hanna et al., 2000; Schneider et al., 1999). Additionally, there was no apparent toxicity or immunostimulation at this low dose. However, the apparent lack of or reduced toxicity also was surprising and unexpected, given the propensity of HSV infection to cause arterial thrombosis in experimental systems (Key et al., 1990), as well as the indication that HSV may actually be involved in atherogenesis [Alber et al., Circ. 102:779–785, 2000].

In certain embodiments, HSV-1 vectors and methods of use described herein possess high efficiency (e.g., greater than 40% transfection of cells) at low concentrations (e.g., less than about $10^9$ pfu per ml of administered vector). In particular, the HSV-1 vectors described herein allow for reduced viral loads (e.g., a total viral load of less than about $10^{10}$ pfu per ml).

In some embodiments, the HSV-1 vectors and methods of use described herein demonstrate long duration (e.g., greater than about 28 days) of transgene expression in a host cell, tissue, or organism. In particular aspects, the transgene duration is prolonged in despite the fact that the host organism is immunocompetent.

In particular embodiments, the HSV-1 vectors and methods of use described herein demonstrate a high level of cell penetrance (e.g., greater than about 40%).

In certain embodiments, the HSV-1 vectors and methods of use described herein demonstrate low or acceptable cytotoxicity (e.g., less than about 10% cytotoxicity at a multiplicity of infection (MOI) ratio expressed as the total viral particles per cell of 2).

A. Nucleic Acids

Certain embodiments of the present invention concern various nucleic acids, including vectors, promoters, therapeutic nucleic acids, and other nucleic acid elements that are involved in transformation and expression in cells. In certain aspects, a nucleic acid comprises a wild-type or a mutant nucleic acid. In particular aspects, a nucleic acid encodes a polypeptide or comprises a transcribed nucleic acid.

The term "nucleic acid" is well known in the art. A "nucleic acid" as used herein will generally refer to a molecule (i.e., a strand) of DNA, RNA or a derivative or analog thereof, comprising a nucleotide. A nucleotide includes, for example, a naturally occurring nucleotide containing a purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleotides in length. The term "polynucleotide" refers to at least one molecule of greater than about 100 nucleotides in length.

These definitions generally refer to a single-stranded molecule, but in specific embodiments will also encompass an additional strand that is partially, substantially, or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single-stranded nucleic acid may be denoted by the prefix "ss", a double-stranded nucleic acid by the prefix "ds", and a triple-stranded nucleic acid by the prefix "ts."

In particular aspects, a nucleic acid encodes an RNA and/or a protein, polypeptide, and/or peptide. In certain embodiments, the present invention concerns novel compositions comprising at least one proteinaceous molecule. As used herein, a "proteinaceous molecule," "proteinaceous composition," "proteinaceous compound," "proteinaceous chain," or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above are used interchangeably herein.

A.1. Preparation of Nucleic Acids

A nucleic acid may be made by any technique known to one of ordinary skill in the art, such as, for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite, or phosphoramidite chemistry and solid-phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotides may be used. Various different mechanisms of oligonucleotide synthesis have been disclosed in, for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid includes one produced by enzymes in amplification reactions such as PCR™ (see, for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989).

A.2. Purification of Nucleic Acids

A nucleic acid may be purified on polyacrylamide gels, cesium chloride centrifugation gradients, or by any other means known to one of ordinary skill in the art (see for example, Sambrook et al., 1989. In preferred aspects, a nucleic acid is a pharmacologically acceptable nucleic acid. Pharmacologically acceptable compositions are known to those of skill in the art; exemplars are described herein.

In some embodiments, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of the bulk of cellular components or in vitro reaction components such as, for example, macromolecules such as lipids or proteins, small biological molecules, and the like.

A.3. Nucleic Acid Segments

In certain embodiments, the nucleic acid is a nucleic acid segment. As used herein, the term "nucleic acid segment," is a smaller fragment of a nucleic acid, such as, for non-limiting example, those that encode only part of a peptide or polypeptide sequence. Thus, a "nucleic acid segment" may comprise any part of a gene sequence, of from about 2 nucleotides, and preferably 50 nucldotiedes, to the full length of a peptide or polypeptide encoding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

$$n \text{ to } n+y$$

where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17, and so on. For a 20-mer, the nucleic segments correspond to bases 1 to 20, 2 to 21, 3 to 22, and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

A.4. Nucleic Acid Complements

The present invention also encompasses a nucleic acid that is complementary to a nucleic acid. A nucleic acid "complement(s)" or is "complementary" to another nucleic acid when it is capable of base-pairing with another nucleic acid according to the standard Watson-Crick, Hoogsteen, or reverse Hoogsteen complementarity rules. As used herein "another nucleic acid" may refer to a separate molecule or a spatially separated sequence of the same molecule. In preferred embodiments, a complement is an antisense nucleic acid used to reduce expression (e.g., translation) of a RNA transcript in vivo.

As used herein, the term "complementary" or "complement(s)" also refers to a nucleic acid comprising a sequence of consecutive nucleotides or semi-consecutive nucleotides (e.g., one or more of the consecutive nucleotides is not present in the molecule) capable of hybridizing to another nucleic acid strand or duplex even if less than all the nucldotides do not base pair with a counterpart nucleotide. However, in some antisense embodiments, completely complementary nucleic acids are preferred.

B. Vectors

The term "vector" is used to refer to a carrier nucleic acid molecule into which a nucleic acid sequence can be inserted for introduction into a cell where it can be replicated. As used herein, "vector" refers to both the carrier molecule and a recombinant molecule containing an insert (typically heterologous) nucleic acid and the carrier molecule. The usages will be apparent to one of skill from the context of a recitation. A nucleic acid segment can be "exogenous," which means that it is not a sequence originally from the genome of the cell into which the segment is being introduced. As used herein, a "heterologous" nucleic acid is defined herein to mean a nucleic acid segment that is foreign with respect to another nucleic acid sequence. For example, a nucleic acid segment may be heterologous to the genome of a cell or to another juxtaposed nucleic acid segment that together comprise a larger nucleic acid with the first nucleic acid segment.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described below.

As referred to herein and at a minimum, expression of a heterologous nucleic acid sequence is defined as expression of a cognate RNA molecule (typically an mRNA or rRNA). More generally, expression of a heterologous nucleic acid sequence refers to the cellular processes of transcription and translation that produce a polypeptide gene product. Although the polypeptide gene product would typically include at least one function characteristic of that polypeptide, as referred to herein, expression of a heterologous nucleic acid sequence is further contemplated to include the product of a non-functional polypeptide.

B.1. HSV Viral Vectors

Herpes simplex virus (HSV) type I and type II contain a double-stranded, linear DNA genome of approximately 150 kb, containing at least 84 expressible open reading frames [see Table 1, which sets forth the function of herpes simplex genes (Roizman, *Proc. Natl. Acad. Sci.* 93:11307–11312, October 1996)]. Wild-type HSVs are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Garrido et al., 1999; Lachmann and Efstathiou, 1999), liver (Miytake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or α genes, Early (E) or β genes and Late (L) or γ genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

HSV can infect a wide variety of both dividing and non-dividing host cells, and thus has been used in the production of herpes virus vectors for delivery of heterologous nucleic acids into host cells. In certain embodiments, a herpes simplex virus vector may be a HSV-1 or HSV-2 vector. Particularly preferred vectors are viral vectors that lack one or more copies of a $\gamma_1 34.5$ gene, or ribonucleotide reductase gene (i.e., the $\gamma_1 39$ gene encoding ICP6 or the $\gamma_1 40$ gene). Vectors containing a single copy of the $\gamma_1 34.5$ gene lack the inverted repeat associated with virulence. Viral vectors can be mutated by the methods disclosed herein or as would be known to those of skill in the art to produce a viral vector that lacks at least one $\gamma_1 34.5$ gene and/or ribonucleotide reductase gene for use in the methods disclosed herein. For example, methods of producing herpes virus vectors that lack one or more $\gamma_1 34.5$ genes or ribosomal reductase genes are disclosed in U.S. Pat. Nos. 6,120,773, 6,106,826, 5,795,713, 5,585,096 and 5,328,688, each incorporated herein by reference.

Embodiments would include use (in the methods of the present invention) of herpes simplex viral vectors that are debilitated for growth within the central nervous system. As used herein, a debilitated HSV is defined in the following manner. A wild-type strain (non-recombinant) requires 10 pfu to 1000 pfu to kill a mouse by intracerebral inoculation. A debilitated virus requires at least 100,000 pfu to kill a mouse host. Further, a virulent virus travels from cell to cell in a rapid fashion, while a debilitated virus is highly restricted and does not travel from cell to cell very efficiently (hence more virus particles are required to kill a host such as a mouse), unless the animal host cannot immunologically respond to the infection.

HSV may be debilitated for growth in the CNS and useful in the present methods by a non-silent nucleotide insertion, substitution, or deletion in at least one non-essential gene of a herpes simplex virus. Examples of non-essential genes and their functions are set forth in Table 3. Such a debilitated HSV may alternatively comprise a non-silent nucleotide insertion, substitution, or deletion in at least one essential gene of a herpes simplex virus. Examples of essential genes and their functions are shown in Table 2.

As used herein an essential gene is defined as a gene that is required to produce infectious progeny in a cell. For example, the HSV gene, α4, is essential, i.e., in its absence the virus will not produce infectious progeny. However, one of skill in the art would recognize that a cell line producing the α4 gene product will allow a deletion mutant (α4⁻) to replicate. As used herein a non-essential gene is defined as a gene that, when absent or dysfunctional, does not prevent the virus from replicating and producing progeny in a cell line that does not supply the missing gene product. For example, the HSV gene, α0, is considered non-essential, i.e., an α0 deletion mutant (α0⁻) produces progeny in many different cell lines (in some cell lines the titer is 50–100 fold lower, while in other cell lines nearly normal yields are produced.

To ensure stable modification of genes such as $\gamma_1 34.5$, which are located within the inverted repeat of HSV, the inverted repeat itself is modified sufficiently to prevent reconstitution at the unmodified gene. Without wishing to be bound by theory, it is believed that gene reconstitution, or gene conversion occurs as a result of inverted repeat-mediated pairing of duplicated genes found partially or wholly within the repeat region, with one copy of a gene (e.g., the unmodified copy) serving as a template for conversion of the other copy of the gene (e.g., the modified copy). Accordingly, one of skill, using routine procedures, would modify an inverted repeat in addition to a gene contained therein, sufficiently to prevent the effective loss of the modified gene. For example, one of skill would modify the sequence of one inverted repeat sufficiently to prevent effective in vivo pairing of the repeats and genes they contain, which is expected to prevent the loss of a modified gene found in the repeat, believed to be due to the prevention of gene conversion.

TABLE 1

| GENE | Product | Dispensable in cell culture | Regulation | Function of gene product |
|---|---|---|---|---|
| γ₁34.5 | ICP34.5 | Y | γ₁ | Null mutants are attenuated and fail to block phosphorylation of eIF-2α by activated protein kinase; RNA-dependent kinase; carboxyl terminus homologous to the corresponding domain of the GADD34 proteins. |
| ORF-P | ORF-P | Y | pre α | ORF is antisense to the γ₁34.5 gene and repressed by binding of ICP4 to cap site. Proteins interact with p32, a component of SF2/ASF splicing factor. |
| ORF-O | ORF-O | Y | pre α | Overlaps with ORF-P, a protein made by frameshift from ORF-P. |
| α0 | ICP0 | Y | α | Promiscuous transactivator, requires ICP4 for optimal activity; nucleotidylylated, phosphorylated by $U_L13$, nuclear (early) and cytoplasmic (late) phases. Null mutants debilitated at low multiplicities of infection. |
| $U_L1$ | gL | N | γ | Complex with gH required for transport of both proteins to plasma membrane and for viral entry mediated by gH. |
| $U_L2$ | | Y | β | Uracil DNA glycosylase. |
| $U_L3$ | | Y | γ₂ | Nuclear phosphoprotein of unknown function. Reported to localize to perinuclear region early and to the nucleus late in infection. |
| $U_L4$ | | Y | Unknown | Unknown. |
| $U_L5$ | | N | β | Forms complex with $U_L8$ and $U_L52$ proteins. |
| $U_L6$ | | N | Unknown | Virion protein; required for DNA cleavage and packaging. |
| $U_L7$ | | N | Unknown | Unknown. |
| $U_L8$ | | N | β | Forms complex with $U_L5$ and $U_L52$ (helicase/primase complex). Stabilizes interaction between primers and DNA template. |
| $U_L9$ | | N | γ(?) | Binds to origins of DNA synthesis in sequence-specific (origin) fashion; carries out helicase and ATPase activities. |
| $U_L10$ | gM | Y | γ | Glycoprotein present in virions and plasma membranes. |
| $U_L10.5$ | | ? | Unknown | Unknown. |
| $U_L11$ | | Y | γ(?) | Myristoylated protein; necessary for efficient capsid envelopment and exocytosis. |
| $U_L12$ | | Y | β | Exonuclease (DNase) involved in viral nucleic acid metabolism; reported to localize in nucleoli and in virally induced nuclear dense bodies and to bind to a sequence along with other unidentified proteins. Complex may be involved in cleavage/packaging of viral DNA. |
| $U_L12.5$ | | Y | Unknown | Nuclease-associated with capsids. |
| $U_L13$ | | Y | γ | Virion (nuclear) protein kinase; substrates include ICP0, ICP22, vhs, $U_L3$, $U_L49$, etc. |
| $U_L14$ | | N | Unknown | Unknown. |
| $U_L15$ | | N | γ | ts mutant DNA+. Two exons; protein required for cleavage/packaging of DNA. |
| $U_L16$ | | Y | Unknown | Virion protein; gene located within intron of $U_L15$. |
| $U_L17$ | | N | γ | Located within intron of $U_L15$. |
| $U_L18$ | VP23 | N | γ | Protein required for capsid formation and cleavage/packaging of DNA. |
| $U_L19$ | VP5, ICP5 | N | γ₁ | Major capsid protein. |
| $U_L20$ | | Y | γ | Membrane protein, associates with nuclear membranes, Golgi stacks, etc. Essential for viral exocytosis. |
| $U_L20.5$ | | | γ₂ | Unknown. |
| $U_L21$ | | Y | Unknown | Nucleotidylylated phosphoprotein; unknown function. |
| $U_L22$ | gH | N | γ² | Forms complex with gL (see above). Required for entry, egress, and cell-cell spread. |
| $U_L23$ | ICP36 | Y | β | Thymidine (nucleoside) kinase. |
| $U_L24$ | | Y | γ | Syn locus; membrane-associated protein? |
| $U_L25$ | | N | γ | Virion protein reported to be required for packaging of cleaved viral DNA. |
| $U_L26$ | | N | γ | Serine protease; substrates are $U_L26$ protein and $U_L26.5$ (IC35). (C portion of $U_L26$), VP24 (N terminus of protease) are products of the self-cleavage of $U_L26$. |
| $U_L26.5$ | ICP35 | N | γ | Substrate of $U_L26$ protease unique to B capsids and forms inner core or scaffolding; the precursor, ICP35b,c is cleaved to e, f. On packaging of DNA it is removed from capsid shell. |
| $U_L27$ | gB, VP7 | N | γ¹ | Glycoprotein required for viral entry; forms a dimer and induces neutralizing antibody. A syn locus maps to the carboxyl terminus. |
| $U_L27.5$ | | ? | Unknown | Unknown, antisense to gB. |
| $U_L28$ | ICP18.5 | N | γ | $M_r$ 87–95 K protein required for DNA cleavage/packaging. |
| $U_L29$ | ICP8 | N | β | Binds single-stranded DNA cooperatively, required for viral DNA replication: forms complex with DNA polymerase and $U_L42$. ts mutants are DNA and hence expression of early and late genes may be affected positively or negatively by ICP8. Because ICP8 denatures DNA, it affects renaturation of complementary strands of DNA and affects homologous pairing and strand transfer. |
| $U_L30$ | | N | β | DNA polymerase; forms complex with ICP8 and C terminal 247 amino acids of $U_L42$. |
| $U_L31$ | | N | γ² | Nucleotidylylated phosphoprotein, cofactorinates with nuclear matrix. |
| $U_L32$ | | N | γ² | Cytoplasmic/nuclear protein required for DNA cleavage/packaging. |
| $U_L33$ | | N | Unknown | DNA packaging; necessary for assembly of capsids containing DNA. |
| $U_L34$ | | N | Unknown | Abundant nonglycosylated, membrane-associated, virion protein phosphorylated by $U_S3$. |
| $U_L35$ | VP26 | N | γ² | Basic phosphorylated capsid protein. |
| $U_L36$ | ICPI-2 | N | γ² | Tegument phosphoprotein. DNA is not released from capsids at nuclear pores in cells infected with ts mutant. Reported to form complex with a $M_r$ 140 K protein that binds a sequence DNA. |
| $U_L37$ | ICP32 | N | γ | Cytoplasmic phosphoprotein; in presence of ICP8 it is transported to nucleus and associates with DNA, but phosphorylation is not dependenent on ICP8. Required for maturation of virions. |
| $U_L38$ | VP19C | N | γ² | Capsid assembly protein, blinds DNA and may be involved in anchoring DNA in the capsid. |
| $U_L39$ | ICP6 | Y | β | Large subunit of ribonucleotide reductase. Autophosphorylates via unique N terminus but does not trans-phosphorylate. |
| $U_L40$ | | Y | β | Small subunit of ribonucleotide reductase. |
| $U_L41$ | VHS | Y | γ | Causes nonspecific degradation of mRNA after infection; shuts off host protein synthesis, enables sequential synthesis of viral proteins. |
| $U_L42$ | | N | β | Double-stranded DNA-binding protein, binds to and increases processivity of DNA polymerase. |
| $U_L43$ | | Y | Unknown | Amino acid sequence predicts membrane-associated protein. |
| $U_L43.5$ | | Y | | Antisense to $U_L43$; low abundance nuclear protein; accumulates in assemblons. |

TABLE 1-continued

| GENE | Product | Dispensable in cell culture | Regulation | Function of gene product |
|---|---|---|---|---|
| $U_L44$ | gC, vp7.5 | Y | $\gamma^2$ | Glycoprotein involved in cell attachment; required for attachment to the apical surface of polarized MDCK cells. |
| $U_L45$ | | Y | $\gamma^2$ | Encodes a $M_1$ 18 K protein of unknown function. |
| $U_L46$ | VP11/12 | Y | $\gamma$ | Tegument phosphoprotein reported to modulate the activity of $U_L48$ (aTIF). |
| $U_L47$ | VP13/14 | Y | $\gamma^2$ | Nucleotidylylated tegument phosphoprotein modulates the activity of $U_L48$ (aTIF). |
| $U_L48$ | VP16, ICP25, □TIF | N | $\gamma$ | Tegument protein, induces $\gamma$ genes by interacting with OctI. The complex binds to specific sequences with the consensus GyATGnTAATGArATTCyTTGnGGG-NC. |
| $U_L49$ | VP22 | N | $\gamma$ | Nucleotidylylated, mono(ADP-ribosyl)ated tegument phosphoprotein. |
| $U_L49.5$ | | N | $\gamma^2$ | Sequence predicts a $M_r$ 12,000 membrane-associated protein. |
| $U_L50$ | | Y | $\beta$ | dUTPase. |
| $U_L51$ | | Y | $\gamma$ | Unknown. |
| $U_L52$ | | N | $\beta$ | Component of the helicase/primase complex. |
| $U_L53$ | gK | Y | $\gamma$ | Glycoprotein required for efficient viral exocytosis; contains syn locus. |
| $\alpha 27$ | ICP27 | N | $\alpha$ | Nucleotidylylated multifunctional regulatory protein; causes redistribution of snRNPs, inhibits RNA splicing. It is required for late gene expression, and negatively regulates early genes. |
| $U_L55$ | | Y | Unknown | Unknown. |
| $U_L56$ | | Y | Unknown | Nuclear, virion-associated protein of unknown function. |
| $\alpha 4$ | ICP4 | N | $\alpha$ | Nucleotidylylated, poly(ADP-ribosyl)ated phosphoprotein; regulates postively most $\beta$ and $\gamma$ genes and negatively itself, ORF-P and the $\alpha 0$ gene; blocks apoptosis. Binds to DNA in sequence specific fashion. |
| $\alpha 22$ | ICP22 | Y | $\alpha$ | Nucleotidylylated regulatory protein, phosphorylated by $U_L13$ and $U_S3$ protein kinases, required for optimal expression of ICP0 and of a subset of $\gamma$ proteins. |
| $U_s1.5$ | $U_s1.5$ | Y | $\alpha$ | Regulatory protein; extent to which it shares function with ICP22 not known. |
| $U_S2$ | | Y | Unknown | Unknown. |
| $U_S3$ | | Y | $\beta$ | Protein kinase; major substrate is $U_L34$ protein. |
| $U_S4$ | gG | Y | $\gamma$ | Glycoprotein involved in entry, egress, and spread from cell to cell. |
| $U_S5$ | gJ(?) | Y | Unknown | Sequence predicts glycoprotein. |
| $U_S6$ | gD VP17/18 | N | $\gamma_1$ | Glycoprotein required for post-attachment entry of virus into cells. |
| $U_S7$ | gI | Y | $\gamma$ | gI and gE glycoproteins form complex for transport to plasma membrane and also to constitute a high-affinity Fc receptor. GI is required for basolateral spread of virus in polarized cells. |
| $U_S8$ | gE | Y | $\gamma_2$ | FC receptor; involved in basolateral spread of virus in polarized cells. |
| $U_S8.5$ | | Y | $\beta$ or $\gamma_1$ | Unknown. |
| $U_S9$ | | Y | Unknown | Tegument protein phosphorylated by $U_L13$. |
| $U_S10$ | | Y | Unknown | Tegument protein. |
| $U_S11$ | | Y | $\gamma_2$ | Tegument protein binds to $U_L34$ mRNA in sequence- and conformation-specific fashion; binds to the 60S ribosomal subunit and localizes in the nucleolus. |
| $\alpha\square 47$ | ICP47 | Y | $\gamma$ | Binds to TAP1/TAP2 and to block antigen presentation to CD8+ cells. |
| OrisTU | OrisRNA | Y | $\gamma_2$ | RNA transcribed across S origins of DNA synthesis. Function is not known. |
| LATU | LATs | Y | pre $\alpha$? | Transcripts, found in latently infected neurons. Function is not known. |

TABLE 2

EXEMPLARY ESSENTIAL HSV GENES

| Group | Number of Genes | Function (Genes) |
|---|---|---|
| 1 | 4 | Virus attachment, penetration, envelopment, and exocytosis, (gB, gD, gH, gL) |
| 2 | 2 | Regulation of gene expression: $\alpha 4$: positive and negative control of gene expression $\alpha 27$: post transcriptional processing, transport of RNA. |
| 3 | 7 | Replication of viral DNA ($U_L5$, 8, 9, 29, 30, 42, 52) |
| 4 | 8 | Capsid proteins including the protease ($U_L6$, 17, 18, 19, 26, 26.5, 35, 38) |
| 5 | 6 | Packaging of DNA ($U_L15$, 25, 28, 31, 32, 33) |
| 6 | 10 | Virion assembly and other functions ($U_L7$, 14, 27.5, 34, 36–38, 48, 49, 49.5) |

TABLE 3

EXEMPLARY NON-ESSENTIAL HSV GENES

| Group | Number of Genes | Function (Genes) |
|---|---|---|
| 1 | 12 | Entry into polarized cells, sorting, exocytosis: (gC, gE, gG, gI, gJ, gK, gM, $U_L11$, 20, 24, 43, 45) |
| 2 | 4 | Block host response to infection: $\gamma 34.5$ blocks phosphorylation of eIF-2$\alpha$ $\alpha 47$: blocks presentation of antigenic peptides to the immune system. $U_S9$: binds ubiquitin and proteasomes. $U_S3$: protein kinase, blocks apoptosis. |
| 3 | 7 | Enable viral replication in nondividing cells: thymidine kinase, dUTPase, DNase ribonucleotide reductase, uracil glycosylase |
| 4 | 1 | Degrade cellular mRNA and facilitated expression of viral genes. $U_L41$ |
| 5 | 18 | Functions are not known: $U_S2$, 8.5, 10; $U_L3$, 4, 8.5, 9.5, 13, 16, 20.5, 21, 43.5, 46, 47, 51, 55, 56; ICP 22 |
| 6 | 2 | Genes suppressed during productive infection: ORF P: inhibits synthesis of proteins from spliced RNA. ORF O: blocks the ICP4 transactivator from binding DNA. |

As used herein, a viral vector "lacks" a gene when it is mutated so that one or more copies of the mutated gene possess reduced or absent expression or activity sufficient to debilitate it for growth in the central nervous system (CNS)

or neurons as defined above. Such mutations may comprise, for example, frame-shift mutations, insertions, deletions, truncations, and the like in coding or regulatory sequences for one or more genes. The product of the $\gamma_1 34.5$ gene contributes to neurovirulence (Chou et al., 1994). A viral vector that lacks one or more $\gamma_1 34.5$ genes has attenuated neurovirulence, but does not block protein synthesis and will cause the death of normal host cells (of course, deletion of the $\gamma_1 34.5$ gene typically deletes part or all of the overlapping and oppositely oriented orfp. HSV viral vectors that lack one or more ribonucleotide reductase genes also have attenuated neurovirulence (i.e., loss of either subunit of ribonucleotide reductase results in attenuation) and are susceptible to antiviral drugs such as acyclovir and ganciclovir, allowing for antiviral therapy in instances wherein a host exhibits an undesired side effect of vector administration [e.g., viral encephalitis, U.S. Pat. No. 6,106,826]. It is contemplated that one or more other genes in a herpes viral vector may be mutated to improve the efficacy or reduce the side effects of a herpes viral vector. Such genes are known in the art, and include the thymidine kinase (tk) gene, or other genes required for HSV replication, infection or latency.

For use in therapeutic gene delivery, HSV may be replication-defective. Protocols for generating replication-defective HSV helper virus-free cell lines have been described (U.S. Pat. No. 5,879,934; U.S. Pat. No. 5,851,826, each specifically incorporated herein by reference in its entirety). One IE protein, Infected Cell Polypeptide 4 (ICP4), encoded by the $\alpha 4$ gene, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted for ICP4 indicate that such viruses are potentially useful for gene transfer purposes (Krisky et al., 1998a). One property of viruses deleted for ICP4 that makes them desirable for gene transfer is that they only express the five other IE genes: $U_S$ 1.5, ICP0, ICP27, ICP22 and ICP47 (DeLuca et al., 1985) without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevent early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B cell malignancies (Suzuki et al., 1998), ovarian cancer (Wang et al., 1998) and Duchenne Muscular Dystrophy (Huard et al., 1997).

Thus, in some embodiments, a viral vector comprises a nucleic acid sequence that encodes a therapeutic nucleic acid. In preferred aspects, a therapeutic nucleic acid encodes antisense nucleic acid or proteinaceous composition effective to treat a vascular, cardiac, and/or cardiovascular disease or disorder. One of skill in the art would be well equipped to construct a vector through standard recombinant techniques (see, for example, Maniatis et al., 1988 and Ausubel et al., 1994. Non-limiting examples of virus vectors that may be used to deliver a nucleic acid of the present invention are described below.

B.2. Therapeutic Nucleic Acids

In certain embodiments, a vector of the present invention comprises heterologous nucleic acid. In preferred aspects, a heterologous nucleic acid comprises a therapeutic nucleic acid encoding a proteinaceous composition or an antisense product. Exemplary heterologous nucleic acids encode a nucleotide (e.g., antisense), protein, polypeptide or peptide product having an antiproliferative, vasodilatory or angiogenic activity.

The nucleotide and protein, polypeptide and peptide sequences for various genes have been previously disclosed, and may be found at computerized databases known to those of ordinary skill in the art. One such database is the National Center for Biotechnology Information's Genbank and Gen-Pept databases. The coding regions for these known genes may be amplified, cloned into and/or expressed in the vectors of the present invention using the techniques disclosed herein or by any technique that would be know to those of ordinary skill in the art (see, for example, Sambrook et al., 1989).

In certain embodiments, a vector may comprise more than one such therapeutic nucleic acid. The therapeutic nucleic acids could be from the same functional group (e.g., both antiproliferative, vasodilatory or angiogenic, etc.) or from different functional groups (e.g., an antiproliferative and an angiogenic). By presenting particular combinations of therapeutic nucleic acids to a target cell, it may be possible to augment the overall effect of either or both nucleic acids or their encoded products on the physiology of the target cell.

For example, deposits of extracellular matrix proteins and vascular cell proliferation are associated with atherosclerosis. Genes such as acidic fibroblast growth factor (aFGF) that are overexpressed in, e.g., porcine arteries result in smooth muscle cell proliferation and resultant arterial wall thickening, as well as new blood vessel formation in the arterial wall due to endothelial cell migration (Nabel et al, 1993). TGF-$\beta 1$ and platelet-derived growth factor B (PDGFB) overexpression have also led to vessel wall thickening. In certain aspects, it is contemplated that expression, in vascular or cardiovascular cells, of nucleic acids that bind RNAs encoding proteins that contribute to atherosclerosis (e.g., aFGF, TGF-$\beta 1$, PDGFB) will reduce the progress of atherosclerosis.

In another example, it has been demonstrated that administration of a vector that expresses a nucleic acid whose encoded product inhibits cell growth can inhibit restenosis in a patient. For example, an adenoviral vector that expressed thymidine kinase, which makes cells susceptible to killing by ganciclovir, coupled with administration of ganciclovir, prevented smooth muscle proliferation and restenosis in an animal model system after balloon angioplasty (Ohno et al., 1994). Thus, in particular facets, it is contemplated that administration of vectors that express such therapeutic nucleic acids for blood vessel thickening may be combined with administration of a pharmacological agent (e.g., an antihyperlipoproteinemic, an antiarteriosclerotic, an antithrombotic/fibrinolytic agent, an antihypertensive agent) and/or a surgical procedure (e.g., arterial bypass surgery, balloon angioplasty) used in the treatment of patients suffering from atherosclerosis or restenosis.

In preferred embodiments, the therapeutic nucleic acid will be effective in treating a vascular or cardiovascular disease or condition. A cardiovascular disease or condition which may benefit from administration of a vector of the present invention includes, but is not limited to, chronic heart failure, hypertensive cardiovascular disease, ischemic heart disease, arrhythmia, congenital heart disease, valvular heart disease or stenotic defect, cardiomyopathy, aneurysm, chronic venous insufficiency, peripheral arterial disease or a combination thereof.

In certain embodiments, a vector of the present invention may encode at least one antiproliferative, vasodilatory or angiogenic proteinaceous composition. For example, in certain aspects, a vector of the present invention may comprise an antithrombotic nucleic acid, a nucleic acid that regulates angiogenesis (e.g., VEGF, aFGF, bFGF), an immunomodulatory nucleic acid (e.g., angiostatin, endostatin, TNFα, IL-1, IL-10), a cell proliferation stimulatory nucleic acid (e.g., platelet-derived growth factor, ras, c-myc, c-fos), a nucleic acid that encodes an inhibitor of cell proliferation (e.g., p53, p21, retinoblastoma protein (Rb)) or antisense expressing constructs of such nucleic acids.

In further embodiments, a vector of the present invention may encode one or more enzymes, including, but not limited to, angiogenin, proliferating cell nuclear antigen (PCNA), senescent cell-derived inhibitor 1 (sdi1), a cell cycle division protein (cdc), a cyclin-dependent kinase (cdk), C-type natriuretic peptide (CNP); a homeobox gene including, but not limited to, gax, thymidine kinase (tk), cytosine deaminase, endothelial cell nitric oxide synthase (ec-NOS), inducible nitric oxide synthase (iNOS), hirudin; a cell-adhesion molecule including, but not limited to, VCAM, ICAM, PECAM or E-selectin; a tissue inhibitor of a metalloproteinase (TIMP); analogs to cAMP such as adrenomedulin, mitogen-activated protein kinases (MAPKs) such as extracellular response kinases (ERKs) and c-jun N-terminal kinase (JNK) and their inhibitors, and their antisense oligonucleotides or polypeptides. In other embodiments, a vector of the present invention may encode one or more polynucleotides. In other embodiments, a vector of the present invention may comprise an oncogene including, but not limited to, c-myb.

B.2.a. Antithrombotic Nucleic Acids

In certain embodiments, a therapeutic nucleic acid may produce an anti-thrombotic effect. Non-limiting examples of such nucleic acids include those that encode COX-1, TFPI, PGS, Dp, ras, myc, neu, raf, erb, fms, trk, ret, gsp, hst, abl, E1A, hirudin, t-PA or p300 coding sequences.

B.2.b. Angiogenesis-Regulating Nucleic Acids

In other embodiments, a vector of the present invention may encode a nucleic acid that increases or inhibits angiogenesis. Non-limiting examples of nucleic acids that may regulate angiogenesis include vascular endothelial growth factor (VEGF), acidic fibroblast growth factor (aFGF), basic fibroblast growth factor (bFGF), thrombospondin, BAI-1, GDAIF, TNFα, or their receptors.

B.2.c. Immunomodulators

It is contemplated that immunomodulators can be included in the vector to augment a cell's or a patient's (e.g., an animal's) response. Immunomodulators can be included as purified proteins, nucleic acids encoding immunomodulators, and/or cells that express immunomodulators in a vaccine composition. The following sections list non-limiting examples of immunomodulators that are of interest, and it is contemplated that various combinations of immunomodulators may be used in certain embodiments (e.g., a cytokine and a chemokine).

B.2.c.i. Cytokines

Interleukins, cytokines, nucleic acids encoding interleukins or cytokines, and/or cells expressing such compounds are contemplated as heterologous nugleic acid gene products. Interleukins and cytokines, include, but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH-1, METH-2, tumor necrosis factor (TNF; Cachectin), TGFβ, LT and combinations thereof.

B.2.c.ii. Chemokines

Chemokines, nucleic acids that encode for chemokines, and/or cells that express such also may be used as heterologous nucleic acids. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to a site of treatment, e.g., invascular tissue. Such chemokines include, for example, RANTES, MCAF, MCP-1, MIP1-alpha, IL-8, MIP1-Beta, IP-10 and combinations thereof. The skilled artisan will recognize that certain cytokines are also known to have chemoattractant effects and could also be classified as chemokines.

B.2.d. Inducers of Cellular Proliferation

In one embodiment of the present invention, it is contemplated that anti sense mRNA directed to a particular inducer of cellular proliferation is used to prevent expression of the inducer of cellular proliferation. The proteins that induce cellular proliferation further fall into various categories dependent on function. The commonality of all of these proteins is their ability to regulate cellular proliferation.

For example, a form of PDGF, the sis oncogene, is a secreted growth factor. The proteins FMS, ErbA, ErbB and neu are also growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein tyrosine kinase, and its transformation from proto-oncogene to oncogene, in some cases, results via mutations at tyrosine residue 527. In contrast, transformation of the GTPase protein ras from proto-oncogene to oncogene, in one example, results from a valine to glycine mutation at amino acid 12 in the sequence, reducing ras GTPase activity.

Other proteins such as Jun, Fos and Myc are proteins that directly exert their effects on nuclear functions as transcription factors.

B.2.e. Inhibitors of Cellular Proliferation

In certain embodiment, the restoration of the activity of an inhibitor of cellular proliferation through a genetic construct is contemplated. Tumor suppressor oncogenes function to inhibit excessive cellular proliferation. The inactivation of these genes destroys their inhibitory activity, resulting in unregulated proliferation. The tumor suppressors p53, p16, p21 and C-CAM are examples of this class of proteins.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue.

Wild-type p53 is recognized as an important growth regulator and a signal transduction protein in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDKs. One CDK, cyclin-dependent kinase 4 (CDK4), regulates progression through $G_1$. The activity of this enzyme may be to phosphorylate Rb at late $G_1$. The activity of CDK4 is controlled by an activating subunit, D-type cyclin, and by an inhibitory subunit, the p16$^{INK4}$, which has been biochemically characterized as a protein that specifically binds to and inhibits CDK4, and thus may regulate retinoblastoma protein (Rb) phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the retinoblastoma protein. p16 also is known to regulate the function of CDK6.

p16$^{INK4}$ belongs to a newly described class of CDK-inhibitory proteins that also includes p16$^B$, p19, p21$^{WAF1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of p16$^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, and p21/p27 fusions.

B.2.f. Regulators of Programmed Cell Death

In certain embodiments, it is contemplated that genetic constructs debilitated for growth, in contrast to wild-type HSV, will stimulate rather than block apoptosis and, thus, will be used to promote the death of diseased or undesired tissue. Apoptosis, or programmed cell death, is an essential process for normal embryonic development, maintaining homeostasis in adult tissues (Kerr et al., 1972). The Bcl-2 family of proteins and the ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists, i.e., apoptosis regulators.

Subsequent to its discovery, it was shown that Bcl-2 acts to suppress cell death triggered by a variety of stimuli. Also, it now is apparent that there is a family of Bcl-2 cell death regulatory proteins that share common structural and sequence homologies. These different family members have been shown to either possess similar functions to Bcl-2 (e.g., BclXL, Bclw, Bcls, Mcl-1, A1, Bfl-1) or counteract Bcl-2 function and promote cell death (e.g., Bax, Bak, Bik, Bim, Bid, Bad, Harakiri). Wild-type HSV blocks apoptosis by a number of mechanisms, including the modification of proapoptotic members of the Bcl-2 family of proteins.

B.3. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcription of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30–110 bp upstream of the start site, although a number of promoters have been shown to contain functional elements downstream of the start site as well. To bring a coding sequence "under the control of" a promoter, one positions the 5' end of the transcription initiation site "downstream" of (i.e., 3') the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter is referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, consensus sequences, and/or mutations that alter expression. For example, prokaryotic promoters that are most commonly used in recombinant DNA constructions include the β-lactamase (penicillinase), lactose and tryptophan (trp) promoter systems.

Preferred promoters and other expression control elements such as enhancers, transcription factor binding sites, RNA splice sites, polyadenylation signals, terminators, ribosome binding sites and the like (see below), are eukaryotic elements functional in vascular cells. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

In some embodiments, the promoter is constitutive. In other embodiments, the promoter is tissue-specific. In preferred aspects, the promoter is vascular or tissue-specific. The identity of tissue-specific promoters or other elements, as well as assays to characterize their activity, are well known to those of skill in the art. Nonlimiting examples of such elements useful in eukaryotic cells (e.g., mammalian cells) include the SM22 gene promoter (Kuhbandner et al., 2000), human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

Additionally, any promoter/enhancer combination (for example, the Eukaryotic Promoter Data Base EPDB, accessed via the Internet) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Table 4 lists non-limiting examples of elements/promoters that may be employed, in the context of the present invention, to regulate the expression of a gene. Table 5 provides non-limiting examples of inducible elements, which are regions of a nucleic acid sequence that can be activated in response to a specific stimulus.

TABLE 4

Promoter and/or Enhancer

| Promoter/Enhancer | References |
|---|---|
| Immunoglobulin Heavy Chain | Banerji et al., Cell 35:729, 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., Mol. Cell. Biol. 7:2256, 1987] |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α₁-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., Cell 27:299, 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |

TABLE 4-continued

Promoter and/or Enhancer

| Promoter/Enhancer | References |
|---|---|
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., Cell 59:273, 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 5

Inducible Elements

| Element | Inducer | References |
|---|---|---|
| MTII | Phorbol Ester (TFA) Heavy metals | Palmiter et al., 1982; Haslinger et al., 1985; Searle et al., 1985; Stuart et al., 1985; Imagawa et al., 1987; Karin et al., 1987; Angel et al., Cell 49:729, 1987; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakaiet al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., Mol. Cell. Biol. 7:2256, 1987 |
| Stromelysin | Phorbol Ester (TPA) | Angel et al., Cell 49:729, 1987 |
| SV40 | Phorbol Ester (TPA) | Angel et al., Cell 49:729, 1987 |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

B.4. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic.

In certain embodiments of the invention, the use of internal ribosome entry sites (IRES) elements are used to create multigene, or polycistronic, messages. IRES elements are able to bypass the ribosome scanning model of 5′ methylated Cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

B.5. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with a type II restriction endonuclease that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments. Techniques involving restriction enzymes and ligation reactions are well known to those of skill in the art of recombinant technology.

B.6. Splicing Sites

Most transcribed eukaryotic RNA molecules will undergo RNA splicing to remove introns from the primary transcripts. Because HSV blocks RNA splicing, cDNAs are the preferred form of eukaryotic insert in the vector, although genomic sequences properly expressible (e.g., intron-free) are also contemplated. Vectors lacking the RNA splice-blocking capacity of wild-type HSV may still require donor and/or acceptor splicing sites to ensure proper processing of the transcript for protein expression (see, for example, Chandler et al., 1997, herein incorporated by reference.)

B.7. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read-through from a cassette containing a heterologous nucleic acid into other sequences.

Terminators contemplated for use in the invention include any known terminator of transcription described herein or known to one of ordinary skill in the art including, but not limited to, the termination sequences of genes, such as for example the bovine growth hormone terminator or viral termination sequences, such as the SV40 terminator. In certain embodiments, termination may be due to a lack of transcribable or translatable sequence, such as due to a sequence truncation.

B.8. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

B.9. Origins of Replication

In order to propagate a vector in a host cell, the vector may contain one or more origins of replication sites (often termed "ori"), which is a specific nucleic acid sequence at which replication is initiated. Alternatively, an autonomously replicating sequence (ARS) is employed if the host cell is yeast.

B.10. Selectable and Screenable Markers

In certain embodiments of the invention, cells containing a nucleic acid construct of the present invention may be identified in vitro or in vivo by including a marker in the expression vector. Such markers confer an identifiable phenotypic change to the cell permitting easy identification of cells containing the expression vector. For example, a screenable marker (e.g., β-galactosidase) may be used to identify transformed cells.

Generally, a selectable marker is one that confers a property that allows for selective survivability. A positive selectable marker is one in which the presence of the marker allows for survival under certain known conditions (e.g., antibiotic challenge), while a negative selectable marker is one in which its presence prevents survival. An example of a positive selectable marker is a drug (e.g., an antibiotic) resistance marker.

Usually the inclusion of a drug selection marker aids in the cloning and identification of transformants. For example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers, including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the heterologous nucleic acid encoding a gene product. Further examples of selectable and screenable markers are well known to one of skill in the art.

C. Vector Delivery and Cell Transformation

Suitable methods for nucleic acid delivery for transformation of an organelle, a cell, a tissue or an organism for use with the current invention are believed to include virtually any method by which a herpes virus vector can be introduced into an organelle, a cell, a tissue or an organism, as described herein or as would be known to one of ordinary skill in the art. Such methods include, but are not limited to, direct delivery of a nucleic acid such as by ex vivo transfection (Wilson et al., 1989, Nabel et al, 1989), injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789, 215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome-mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Patent Application Publication Nos. WO 94/09699 and 95/06128; U.S. Pat. Nos. 5,610,042; 5,322,783 5,563,055, 5,550,318, 5,538,877 and 5,538,880, and each incorporated herein by reference), and any combination of such methods. Through the application of techniques such as these, organelle(s), cell(s), tissue(s) or organism(s) may be stably or transiently transformed.

C.1. Ex Vivo Transformation

Methods for transfecting vascular cells and tissues removed from an organism in an ex vivo setting are known to those of skill in the art. For example, canine endothelial cells have been genetically altered by retroviral gene transfer in vitro and transplanted into a canine (Wilson et al., 1989). In another example, yucatan minipig endothelial cells were transfected by a retrovirus in vitro and transplanted into an artery using a double-balloon catheter (Nabel et al., 1989). Thus, it is contemplated that cells or tissues may be removed and transfected ex vivo using a herpes virus vector of the present invention. In particular aspects, the transplanted cells or tissues may be placed into an organism. In preferred facets, a therapeutic nucleic acid is expressed in the transplanted cells or tissues.

C.2. Injection

In certain embodiments, a nucleic acid may be delivered to an organelle, a cell, a tissue or an organism via one or more injections (i.e., a needle injection), such as, for example, subcutaneously, intradermally, intramuscularly, intravenously, intraperitoneally, and the like. Methods of injection are well known to those of ordinary skill in the art (e.g., injection of a composition comprising a saline solution), and additional examples are described herein.

C.3. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome. A preferred delivery vehicle comprises a liposome and a ligand selective or, more preferably, specific for a vascular cell-specific binding partner such as a receptor.

C.4. Receptor-Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene-targeting vehicles comprise a cell receptor-specific ligand and a nucleic acid binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome, as described above. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle is a liposome itself, which will preferably comprise one or more lipids or glycoproteins that direct cell-specific binding. For example, lactosyl-ceramide, a galactose-terminal asialganglioside, have been incorporated into liposomes and observed to result in an increase in the uptake of the insulin gene by hepatocytes (Nicolau et al., 1987). It is contemplated that the tissue-specific transforming constructs of the present invention are specifically delivered into a target cell in a similar manner.

D. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell (preferred, with vascular cells being particularly preferred), and it includes any transformable organism that is capable of replicating a vector and/or expressing a heterologous nucleic acid encoded by a vector. A host cell can, and has been, used as a recipient for vectors. A host cell may be "infected," "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as a vector, has been introduced. Therefore, recombinant cells are distinguishable from naturally occurring cells which do not contain a non-native introduced nucleic acid.

Some vectors may employ control sequences that allow it to be replicated and/or expressed in either or both prokaryotic and eukaryotic cells. One of skill in the art would further understand the conditions under which to incubate all of the above-described host cells to maintain them and to permit replication of a vector (e.g., a herpes virus vector of the invention). Also understood and known are techniques and conditions that would allow large-scale production of vectors, as well as production of the nucleic acids encoded by vectors and their cognate polypeptides, proteins, or peptides.

Numerous cell lines and cultures are available for use as a host cell, and may be obtained through the American Type Culture Collection (ATCC). An appropriate host can be determined by one of skill in the art based on the vector backbone (i.e., the carrier) and the desired result. Examples of eukaryotic host cells for replication and/or expression of a vector include, but are not limited to, HeLa, NIH3T3, Jurkat, 293, Cos, CHO, Saos, and PC12 cells. Many host cells from various cell types and organisms are available and would be known to one of skill in the art.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a vector of the present invention. The tissue may be part of, or separated (e.g., by surgery) from, an organism. In certain aspects, cells or a tissue may be removed from a host, contacted with a vector and/or an agent, and then reimplanted into tissue or organism, thereby achieving specificity in vector targeting of host cells through mechanical means such as surgical intervention. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes cells and all cancers thereof.

The extended duration of expression of a nucleic acid comprised in a herpes virus vector of the present invention in a vascular or a cardiovascular tissue is an advantageous aspect of the present invention. In particular embodiments, a vascular or cardiovascular tissue comprises endothelial cells, smooth muscle cells or adventitial cells. In particular aspects, a vector of the present invention may be expressed in one, two, three or more vascular or cardiovascular cell types, (e.g., endothelial cells, smooth muscle cells or adventitial cells) in any combination of cell types. In certain embodiments, a heterologous nucleic acid sequence may be expressed in a vascular or cardiovascular tissue or cell type for a time greater than or equal to about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100 or more days, and any range derivable therein.

In certain embodiments, the host cell or tissue may be found in at least one organism. In certain embodiments, the organism may be, but is not limited to, an eukaryote (e.g., an animal, a human), as would be understood by one of ordinary skill in the art.

E. Therapeutic Agents

In order to increase the effectiveness of a herpes virus vector of the present invention, it may be desirable to combine these compositions and methods of the invention with an agent effective in the treatment of vascular or cardiovascular disease or disorder. In some embodiments, it is contemplated that a conventional therapy or agent including, but not limited to, a pharmacological therapeutic agent, a surgical procedure or a combination thereof, may be combined with vector administration. In a non-limiting example, a therapeutic benefit comprises reduced hypertension in a vascular tissue, or reduced restenosis following vascular or cardiovascular intervention, such as occurs during a medical or surgical procedure. Thus, in certain embodiments, a therapeutic method of the present invention may comprise administration of a vector of the present invention in combination with another therapeutic agent.

This process may involve contacting the cell(s) with an agent(s) and the vector at the same time (e.g., substantially simultaneously) or within a period of time wherein separate administration of the vector and an agent to a cell, tissue or organism produces a desired therapeutic benefit. The terms "contacted" and "exposed," when applied to a cell, tissue or organism, are used herein to describe the process by which a therapeutic construct of the invention and/or therapeutic agent are delivered to a target cell, tissue or organism or are placed in direct contact with the target cell, tissue or organism. The cell, tissue or organism may be contacted (e.g., by administration) with a single composition or pharmacological formulation that includes both a vector of the present invention and one or more agents, or by contacting the cell with two or more distinct compositions or formulations, wherein one composition includes a vector and the other includes one or more agents.

The herpes virus vector may precede, be co-adminstered with, and/or follow the other agent(s) by intervals ranging from minutes to weeks. In embodiments where the vector and other agent(s) are applied separately to a cell, tissue or organism, one would generally ensure that a significant period of time did not expire between the time of each delivery, such that the vector and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the vector. In other aspects, one or more agents may be administered substantially simultaneously with, or about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1 week, about 2 weeks, about 3 weeks, about 4 weeks, about 5 weeks, about 6 weeks, about 7 weeks, about 8 weeks, about 1 month, about 2 months, about 3 months, about 4 months, about 5 months, about 6 months, about 7 months, about 8 months, about 9 months, about 10 months, about 11 months, or about 12 months, and any range derivable therein, prior to and/or after administering the vector of the present invention.

Various combination regimens of the herpes virus vectors of the present invention and one or more agents may be employed. Non-limiting examples of such combinations are shown below, wherein a composition comprising a vector is "A" and an agent is "B":

A/B/A B/A/B B/B/A A/A/B A/B/B B/A/A A/B/B/B B/A/ B/B B/B/B/A B/B/A/B A/A/B/B A/B/A/B A/B/B/A B/B/ A/A B/A/B/A B/A/A/B A/A/A/B B/A/A/A A/B/A/A A/A/ B/A

Administration of the composition comprising a vector to a cell, tissue or organism may follow general protocols for the administration of vascular or cardiovascular therapeutics, taking into account the toxicity of the therapeutic, if any. It is expected that the treatment cycles would be repeated as necessary. It is contemplated that various additional agents may be applied in any combination with the present invention.

E.1. Pharmacological Therapeutic Agents

Pharmacological therapeutic agents and methods of administration, dosages, and the like are well known to those of skill in the art (see for example, the "Physicians Desk Reference," Goodman & Gilman's "The Pharmacological Basis of Therapeutics," "Remington's Pharmaceutical Sciences," and "The Merck Index, Eleventh Edition," incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an anti-infection agent (e.g., an antibacterial agent, an anti-fungal agent, an anti-viral agent) or a combination thereof.

E.1.a. Antihyperlipoproteinemics

In certain embodiments, administration of an agent that lowers the concentration of one of more blood lipids and/or lipoproteins, known herein as an "antihyperlipoproteinemic," may be combined with administration of a vector for cardiovascular therapy, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequestrant, a HMG CoA reductase inhibitor, a nicotinic acid derivative, a thyroid hormone or thyroid hormone analog, a miscellaneous agent (see below) other antihyperlipoproteinemics known in the art, or a combination thereof.

E.1.a.i. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

E.1.a.ii. Resins/Bile Acid Sequestrants

Non-limiting examples of resins/bile acid sequestrants include cholestyramine (cholybar, questran), colestipol (colestid) and polidexide.

E.1.a.iii. HMG CoA Reductase Inhibitors

Non-limiting examples of HMG CoA reductase inhibitors include lovastatin (mevacor), pravastatin (pravochol) or simvastatin (zocor).

E.1.a.iv. Nicotinic Acid Derivatives

Non-limiting examples of nicotinic acid derivatives include nicotinate, acepimox, niceritrol, nicoclonate, nicomol and oxiniacic acid.

E.1.a.v. Thyroid Hormones and Analogs

Non-limiting examples of thyroid hormones and analogs thereof include etoroxate, thyropropic acid and thyroxine.

E.1.a.vi. Miscellaneous Antihyperlipoproteinemics

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5, 8, 11, 14, 17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

E.1.b. Antiarteriosclerotics

A non-limiting example of an antiarteriosclerotic is pyridinol carbamate.

E.1.c. Antithrombotic/Fibrinolytic Agents

In certain embodiments, administration of an agent that aids in the removal or prevention of blood clots may be combined with administration of a vector for cardiovascular therapy, particularly in treatment of athersclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, aspirin and warfarin (coumadin), are preferred.

E.1.c.i. Anticoagulants

Non-limiting examples of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

E.1.c.ii. Antiplatelet Agents

Non-limiting examples of antiplatelet agents include aspirin, a dextran, dipyridamole (persantin), heparin, sulfinpyranone (anturane) and ticlopidine (ticlid).

E.1.c.iii. Thrombolytic Agents

Non-limiting examples of thrombolytic agents include tissue plasminogen activator (activase), plasmin, prourokinase, urokinase (abbokinase), streptokinase (streptase), and anistreplase/APSAC (eminase).

E.1.d. Blood Coagulants

In certain embodiments wherein a patient is suffering from a hemorrhage or an increased likelihood of hemorrhaging, an agent that may enhance blood coagulation may be used. Non-limiting examples of a blood coagulation-promoting agent include thrombolytic agent antagonists and anticoagulant antagonists.

E.1.d.i. Anticoagulant Antagonists

Non-limiting examples of anticoagulant antagonists include protamine and vitamin K1.

E.1.d.ii. Thrombolytic Agent Antagonists and Antithrombotics

Non-limiting examples of thrombolytic agent antagonists include aminocaproic acid (amicar) and transexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

E.1.e. Antiarrhythmic Agents

Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrhythmic agents (calcium channel blockers) and miscellaneous antiarrythmic agents (see below).

E.1.e.i. Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrhythmic agents include encainide (enkaid) and flecainide (tambocor).

E.1.e.ii. Beta Blockers

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

E.1.e.iii. Repolarization Prolonging Agents

Non-limiting examples of an agent that prolong repolarization, also known as a Class III antiarrhythmic agent, include amiodarone (cordarone) and sotalol (betapace).

E.1.e.iv. Calcium Channel Blockers/Antagonist

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazine derivative (e.g., cinnarizine, flunarizine, lidoflazine) or a miscellaneous calcium channel blocker such as bencyclane, etafenone, magnesium, mibefradil or perhexiline. In certain embodiments a calcium channel blocker comprises a long-acting dihydropyridine (nifedipine-type) calcium antagonist.

E.1.e.v. Miscellaneous Antiarrhythmic Agents

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

E.1.f. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

E.1.f.i. Alpha Blockers

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

E.1.f.ii. Alpha/Beta Blockers

In certain embodiments, an antihypertensive agent is both an alpha and beta adrenergic antagonist. A non-limiting example of an alpha/beta blocker is labetalol (normodyne, trandate).

E.1.f.iii. Anti-Angiotension II Agents

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

E.1.f.iv. Sympatholytics

Non-limiting examples of a sympatholytic include a centrally acting sympatholytic or a peripherally acting sympatholytic. Non-limiting examples of a centrally acting sympatholytic, also known as a central nervous system (CNS) sympatholytic, include clonidine (catapres), guanabenz (wytensin) guanfacine (tenex) and methyldopa (aldomet). Non-limiting examples of a peripherally acting sympatholytic include a ganglion-blocking agent, an adrenergic neuron-blocking agent, a β-adrenergic blocking agent or an alpha1-adrenergic blocking agent. Non-limiting examples of a ganglion-blocking agent include mecamylamine (inversine) and trimethaphan (arfonad). Non-limiting examples of an adrenergic neuron-blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blockers include prazosin (minipress), doxazocin (cardura) and terazosin (hytrin).

E.1.f.v. Vasodilators

In certain embodiments, a cardiovascular therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimefylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

E.1.f.vi. Miscellaneous Antihypertensives

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitroprusside, ticrynafen, trimethaphan camsylate, tyrosinase and urapidil.

In certain aspects, an antihypertensive may comprise an arylethanolamine derivative (see below), a benzothiadiazine derivative, a N-carboxyalkyl(peptide/lactam) derivative, a dihydropyridine derivative, a guanidine derivative, a hydrazines/phthalazine, an imidazole derivative, a quaternary ammonium compound, a reserpine derivative or a sulfonamide derivative.

E.1.f.vi.a. Arylethanolamine Derivatives

Non-limiting examples of arylethanolamine derivatives include amosulalol, bufuralol, dilevalol, labetalol, pronethalol, sotalol and sulfinalol.

E.1.f.vi.b. Benzothiadiazine Derivatives

Non-limiting examples of benzothiadiazine derivatives include althizide, bendroflumethazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

E.1.f.vi.c. N-Carboxyalkyl(Peptide/Lactam) Derivatives

Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

E.1.f.vi.d. Dihydropyridine Derivatives

Non-limiting examples of dihydropyridine derivatives include amlodipine, felodipine, isradipine, nicardipine, nifedipine, nilvadipine, nisoldipine and nitrendipine.

E.1.f.vi.e. Guanidine Derivatives

Non-limiting examples of guanidine derivatives include bethanidine, debrisoquin, guanabenz, guanacline, guanadrel, guanazodine, guanethidine, guanfacine, guanochlor, guanoxabenz and guanoxan.

E.1.f.vi.f. Hydrazines/Phthalazines

Non-limiting examples of hydrazines/phthalazines include budralazine, cadralazine, dihydralazine, endralazine, hydracarbazine, hydralazine, pheniprazine, pildralazine and todralazine.

E.1.f.vi.g. Imidazole Derivatives

Non-limiting examples of imidazole derivatives include clonidine, lofexidine, phentolamine, tiamenidine and tolonidine.

E.1.f.vi.h. Quaternary Ammonium Compounds

Non-limiting examples of quaternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

E.1.f.vi.i. Reserpine Derivatives

Non-limiting examples of reserpine derivatives include bietaserpine, deserpidine, rescinnamine, reserpine and syrosingopine.

E.1.f.vi.j. Sufonamide Derivatives

Non-limiting examples of sulfonamide derivatives include ambuside, clopamide, furosemide, indapamide, quinethazone, tripamide and xipamide.

E.1.g. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

E.1.h. Treatment Agents for Congestive Heart Failure

Non-limiting examples of agents for the treatment of congestive heart failure include anti-angiotension II agents, afterload-preload reduction treatment (see below), diuretics and inotropic agents.

E.1.h.i. Afterload-Preload Reduction Treatment

In certain embodiments, an animal (patient) that cannot tolerate an angiotension antagonist may be treated with a combination therapy. Such therapy may combine administration of hydralazine (apresoline) and isosorbide dinitrate (isordil, sorbitrate).

E.1.h.ii. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin sodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxazolamide, furosemide, indapamide, mefruside, methazolamide, piretanide, quinethazone, torasemide, tripamide, xipamide), a uracil (e.g., aminometradine, amisometradine), a potassium-sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexiline, ticrnafen and urea.

E.1.h.iii. Intropic Agents

Non-limiting examples of a positive intropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. A non-limiting example of a phosphodiesterase inhibitor is amrinone (inocor).

E.1.i. Antianginal Agents

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

E.1.j. Anti-Infection Agents

Anti-infection agents (e.g., antibacterials, antifungus, antivirals) are generally used to reduce or prevent infection. Non-limiting examples of antibacterials include antibacterial antibiotics, synthetic antibacterials, leprostatic antibacterials, rickettsia antibacterials, tuberculostatic antibacterials, or a combination thereof.

E.1.j.i. Antibiotic Antibacterials

Non-limiting examples of antibiotic antibacterials include an aminoglycoside (e.g., amikacin, apramycin, arbekacin, a bambermycin, butirosin, dibekacin, dihydrostreptomycin, a fortimicin, gentamicin, isepamicin, kanamycin, micronomicin, neomycin undecylenate, netilmicin, paromomycin, ribostamycin, sisomicin, spectinomycin, streptomycin, streptonicozid, tobramycin), an amphenol (e.g., azidamfenicol, chloramphenicol, chloramphenicol palmitate, chloramphenicol pantothenate, florfenicol, thiamphenicol), an ansamycin (e.g., rifamide, rifampin, rifamycin, rifaximin), a β-lactam (e.g., a carbapenem, a cephalosporin, a cephamycin, a monobactam, an oxacephem, a penicillin), a lincosamide (e.g., clindamycin, lincomycin), a macrolide (e.g., azithromycin, carbomycin, clarithromycin, erythromycin acistrate, erythromycin estolate, erythromycin glucoheptonate, erythromycin lactobionate, erythromycin lactobionate, erythromycin propionate, erythromycin stearate, josamycin, leucomycin, midecamycin, miokamycin, oleandomycin, primycin, primycin, rokitamycin, rosaramicin, roxithromycin, spiramycin, troleandomycin), polypeptides (e.g., amphomycin, bacitracin, capreomycin, colistin, enduracidin, enviomycin, fusagungine, a gramicidin, a gramicidin S, mikamycin, polymyxin, polymyxin B-Methanesulfonic acid, pristinamycin, ristoceitin, teicoplanin, thiostrepton, tuberactinomycin, tyrocidine, tyrothricin, vancomycin, viomycin, viomycin pantothenate, virginiamycin, zinc bacitracin), tetracycline (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin, tetracycline) or a miscellaneous antibiotic antibacterial (e.g., cycloserin, mupirocin, tuberin).

A non-limiting example of a carbapenem β-lactam is imipenem. Non-limiting examples of a cephalosporin β-lactam include cefaclor, cefadroxil, cefamandole, cefatrizine, cefazedone, cefazolin, cefixime, cefinenoxime, cefodizime, cefonicid, cefoperazone, ceforanide, cefotaxime, cefotiam, cefpimizole, cefpiramide, cefpodoxime proxetil, cefroxadine, cefsulodin, ceftazidime, cefteram, cftezole, ceftibuten, ceftizoxime, ceftriaxone, cefuroxime, cefuzonam, cephacetrile sodium, cephalexin, cephaloglycin, cephaloridine, cephalosporin C, cephalothin, cephapirin sodium, cephradine and pivcefalexin. Non-limiting examples of a cephamycin β-lactam include cefbuperazone, cefmetazole, cefminox, cefotetan and cefoxitin. Non-limiting examples of a monobactam β-lactam include aztreonam, carumonam and tigemonam. Non-limiting examples of an oxacephem β-lactam include flomoxef and moxolactam. Non-limiting examples of a penicillin β-lactam include amidinocillin, amidinocillin pivoxil, amoxicillin, ampicillin, apalcillin, aspoxicillin, azidocillin, azlocillin, bacampicillin, benzylpenicillinic acid, benzylpenicillin sodium, carbenicillin, carfecillin sodium, carindacillin, clometocillin, cloxacillin, cyclacillin, dicloxacillin diphenicillin sodium, epicillin, fenbenicillin, floxacillin, hetacillin, lenampicillin, metampicillin, methicillin sodium, mezlocillin, nafcillin sodium, mezlocillin, nafcillin sodium, oxacillin, penamecillin, penethamate hydride, penicillin G benethiamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, talampicillin, temocillin and ticarcillin.

E.1.j.ii. Synthetic Antibacterials

Non-limiting examples of synthetic antibacterials include 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantion), quinolones and quinone analogs (e.g., amifoxacin, cinoxacin, ciprofloxacin, difloxacin, enoxacin, fleroxacin, flumequine, lomefloxacin, miloxacin, nalidixic acid, norfloxacin, ofloxacin, oxolinic acid, pefloxacin, pipemidic acid, piromidic acid, rosoxacin, temafloxacin, tosulfoxacin), sulfonamides (e.g., acetyl sulfamehtoxypraxine, acetyl sulfisoxazole, azosulfamide, benzylsulfamide, choramine-B, chloramine-T, dichloramine T, formosulfathiazole, $N^2$-formylsulfisomidine, $N^4$-β-D-glucosylsulfanilamide, mafenide, 4'-(methylsulfanoyl) sulfanilamide, p-nitrosulfathiazole, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicylic acid, $N^4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole), sulfones (acedapsone, acediasulfone, acetosulfone sodium, dapsone, diathymosulfone, glucosulfone sodium, solasulfone, succisulfone, sulfanilic acid, p-sulfanilylbenzylamine, p,p'-sulfonyldianiline-N, N'diagalactoside, sulfoxone sodium, thiazolsulfone), and miscellaneous synthetic antibacterials (e.g., clofoctol, hexedine, methenamine, methenamine anhydromethylenecitrate, methenamine hippurate, methenamine mandelate, methenamine sulfosalicylate, nitroxoline, and xibornol).

E.1.j.iii. Liprostatic Antibacterials

Non-limiting examples of leprostatic antibacterials include acedapsone, acetosulfone sodium, clofazimine, dapsone, diathymosulfone, glucosulfone sodium, hydnocarpic acid, solasulfone, succisulfone and sulfoxone sodium.

E.1.j.iv. Rickettsia Antibacterials

Non-limiting examples of rickettsia antibacterials, also known as antirickettsials, include p-aminobenzoic acid, chloramphenicol, chloramphenicol palmitate, chloramphenicol pantothenate and tetracycline.

E.1.j.v. Tuberculostatic Antibacterials

Non-limiting examples of tuberculostatic antibacterials include p-aminosalicylic acid, p-aminosalicylic acid hydrazine, benzoylpas, 5-bromosalicylhydroxamic acid, capreomycin, clofazimine, cyacetacide, cycloserine, dihydrostreptomycin, enviomycin, ethambutol, ethionamide, 4'-formylsuccinanilic acid thiosemicarbazone, furonazide, glyconiazide, isobutol, isoniazide, isoniazid methanesulfonate, morphazinamide, opiniazide, parsiniazide, phenyl aminosalicylate, protionamide, pyrazinamide, rifampin, salinazide, streptomycin, subathizone, sulfoniazide, thiacetazone, tiocarlide, tuberactinomycin, tubercidin, tuberin verazide, viomycin and vicmycin pantothenate.

E.1.j.vi. Antifungal Agents

Examples of antifungal agents include antibiotic antifungal agents and synthetic antifungal agents. Non-limiting examples of antibiotic antifungal agents include polyenes, such as amphotericin B, candicidin, dermostatin, filipin, fungichromin, hachimycin, hamycin, lucensomycin, mepartricin, natamycin, nystatin, pecilocin and perimycin; as well as miscellaneous antibiotic antifungal agents such as azaserine, grisofulvin, an oligomycin, neomycin undecylenate, pyrrolnitrin, siccanin, tubercidin and viridin. Examples of synthetic antifungal agents include allylamines, imidazoles, triazoles and miscellaneous synthetic antifungal agents. Non-limiting examples of allylamines include naftifine and terbinafine. Non-limiting examples of imidazoles include bifonazole, butoconazole, chlordantoin, chlormidazole, cloconazole, clotrimazole, econazole, enilconazole, fenticonazole, isoconazole, ketoconazole, miconazole, omoconazole, oxiconazole nitrate, sulconazole and tioconazole. Non-limiting examples of trizoles include fluconazole, itraconazole and terconazole. Non-limiting examples of miscellaneous synthetic antifungal agents include acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, tolciclate, tolindate, tolnaftate, triacetin, ujothion, undecylenic acid and zinc propionate.

E.1.j.vii. Antiviral Agents

Non-limiting example of antiviral agents include certain purines and pyrimidinones, such as acyclovir, cytarabine, dideoxyadenosine, dideoxycytidine, dideoxyinosine, edoxudine, floxuridine, ganciclovir, idoxuridine, inosine pranobex, MADU, trifluridine, vidarabine and zidovudine. Miscellaneous antiviral agents include acetylleucine monoethanolamine, amantadine, amidinomycin, cuminaldehyde, thiosemicarbazone, foscarnet sodium, interferon-α, interferon-β, interferon-γ, kethoxal, lysozyme, methisazone, moroxydine, podophyllotoxin, ribavirin, rimantadine, stallimycin, statolon, tromantadine and xenazoic acid.

E.2. Surgical Procedures

In certain aspects, surgical procedures may be performed along with the administration of the HSV vector, or to facilitate targeting of the vector to vascular cells, tissues and organs. Surgical procedures would include, for example, preventative, diagnostic or staging, curative, and palliative surgery. Surgery, and in particular a curative surgery, may be used in conjunction with other therapies, such as administraion of a growth-debilitated (CNS) HSV vector and one or more other agents.

Such surgical procedures for vascular and cardiovascular diseases and disorders are well known to those of skill in the art, and include, but are not limited to, performing surgery on an organism, providing a cardiovascular mechanical prosthesis, angioplasty, coronary artery reperfusion, catheter ablation, providing an implantable cardioverter defibrillator to the subject, mechanical circulatory support, or a combination thereof. Non-limiting examples of a mechanical circulatory support that may be used in the present invention comprise an intra-aortic balloon counterpulsation, left ventricular assist device or combination thereof.

Of course, further treatment of the area of surgery may be accomplished by perfusion, direct injection, systemic injection or local application of the area with at least one additional therapeutic agent (e.g., a vector for use in the methods of the invention, a pharmacological therapeutic agent), as would be known to one of skill in the art or described herein.

F. Pharmaceutical Preparations

Pharmaceutical compositions of the present invention comprise an effective amount of one or more herpes virus vector(s) or additional agent(s) dissolved or dispersed in a pharmaceutically acceptable carrier. The phrases "pharmaceutical or pharmacologically acceptable" refer to molecular entities and compositions that do not produce an adverse, allergic or other untoward reaction when administered to an animal, such as, for example, a human, as appropriate. The preparation of a pharmaceutical composition that contains at least one herpes virus vector or additional active ingredient will be known to those of skill in the art in light of the present disclosure, as exemplified by Remington's Pharmaceutical Sciences, 18th Ed., Mack Printing Company, 1990, incorporated herein by reference. Moreover, for animal (e.g., human) administration, it will be understood that preparations should meet sterility, pyrogenicity, general safety and purity standards as required by the U.S. FDA Office of Biological Standards or equivalent governmental regulations in other countries, where applicable.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, and like materials and combinations thereof, as would be known to one of ordinary skill in the art (see, for example, Remington's Pharmaceutical Sciences, 18th Ed., Mack Printing Company, 1990, pp.

1289–1329, incorporated herein by reference). Except insofar as any conventional carrier is incompatible with the active ingredient, its use in the therapeutic or pharmaceutical compositions is contemplated.

A pharmaceutical composition comprising a herpes virus vector and/or additional agent(s) may exploit different types of carriers depending on whether it is to be administered in solid, liquid or aerosol form, and whether it need be sterile for such routes of administration as injection. The pharmaceutical compositions can be administered intravenously, intradermally, intraarterially, intra-graft, intraperitoneally, intralesionally, intracranially, intraarticularly, intraprostatically, intrapleurally, intratracheally, intranasally, intravitreally, intravaginally, intrarectally, topically, intratumorally, intramuscularly, intraperitoneally, subcutaneously, subconjunctivally, intravesicularly, mucosally, intrapericardially, intraumbilically, intraocularly, orally, topically, locally, inhalation (e.g. aerosol inhalation), injection, infusion, continuous infusion, localized perfusion bathing target cells directly (e.g., in an autogenous tissue graft), via a catheter, via lavage, in cremes, in lipid compositions (e.g., liposomes), or by any other method or any combination of the foregoing as would be known to one of ordinary skill in the art (see, for example, Remington's Pharmaceutical Sciences, 18th Ed., Mack Printing Company, 1990).

The actual dosage amount of a pharmaceutical composition of the present invention administered to an animal patient can be determined by physical and physiological factors such as body weight, severity of condition, the type of disease being treated, previous or concurrent therapeutic interventions, idiopathy of the patient and the planned route of administration. The practitioner responsible for administration will, in any event, determine the concentration of active ingredient(s) in a pharmaceutical composition and appropriate dose(s) for the individual subject using routine procedures.

In certain embodiments, pharmaceutical compositions may comprise, for example, at least about 0.1% of an active compound (e.g., a herpes virus vector, a therapeutic agent). In other embodiments, the active compound may comprise between about 2% to about 75% of the weight of the unit, or between about 25% to about 60%, for example, and any range derivable therein. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable rang e from the values provi ded herein, a range of about 5 m g/kg body weight to about 100 mg/kg body weight, about 5 microgram/kg body weight to about 500 milligram/kg body weight, etc., can be administered, based on the values disclosed.

In any case, the pharmaceutical composition may comprise various antioxidants to retard oxidation of one or more component. Additionally, the prevention of the action of microorganisms can be brought about by preservatives such as various antibacterial and antifungal agents, including, but not limited to, parabens (e.g., methylparabens, propylparabens), chlorobutanol, phenol, sorbic acid, thimerosal or combinations thereof.

A herpes virus vector and/or an agent may be formulated into a pharmaceutical composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as sodium, potassium, ammonium, calcium or ferric hydroxides; or such organic bases as isopropylamine, trimethylamine, histidine or procaine.

In embodiments where the pharmaceutical composition is in a liquid form, a carrier can be a solvent or dispersion medium including, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid, polyol or lipids; by the use of surfactants such as, for example, hydroxypropylcellulose; or combinations thereof. In many cases, it will be preferable to include isotonic agents, such as sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments, the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known to include drugs such as antibiotics or antihistamines.

In certain embodiments, the viral vector concentration that may be administered is about $10^2$, about $10^3$, about $10^4$, about $10^5$, about $10^6$, about $10^7$, about $10^8$, about $10^9$, to about $10^{10}$ PFU/ml, and any integer derivable therein, and any range derivable therein. In some embodiments, the concentration range of viral vectors that may be administered to a tissue or organism may include from about $10^3$, about $10^4$, about $10^5$, about $10^6$, about $10^7$, about $10^8$, about $10^9$, about $10^{10}$, about $10^{11}$, about $10^{12}$, to about $10^{13}$ PFU/kg, and any integer derivable therein, and any concentration range derivable therein. In other embodiments, the concentration range of viral vectors that may be administered to a cell (MOI) may include from about 0.1, about 0.2, about 0.3, about 0.4, about 0.5, about 0.6, about 0.7, about 0.8, about 0.9, about 1, about 2, about 3, about 4, about 5, about 6, about 7 about 8, about 9, about 10, about 11, about 12, about 13, about 14, about 15, about 16, about 17, about 18, about 19, about 20, about 21, about 22, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, to about 100 PFU/cell, and any range derivable therein.

In certain embodiments, the pharmaceutical composition is prepared for administration by such routes as oral ingestion. In these embodiments, the solid composition may comprise, for example, solutions, suspensions, emulsions, tablets, pills, capsules (e.g., hard- or soft-shelled gelatin capsules), sustained release formulations, buccal compositions, troches, elixirs, suspensions, syrups, wafers, or combinations thereof. Oral compositions may be incorporated directly into the food of the diet. Preferred carriers for oral administration comprise inert diluents, assimilable edible carriers or combinations thereof. In other aspects of the invention, the oral composition may be prepared as a syrup or elixir. A syrup or elixir may comprise, for example, at least one active agent and, optionally, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. The composition may comprise one or more of the following: a binder, such as gum tragacanth, acacia, cornstarch, gelatin or combinations thereof; an excipient, such as dicalcium phosphate, mannitol, lactose, starch, magnesium stearate, cellulose, magnesium carbonate or combinations thereof; a disintegrating agent, such as corn starch, potato starch, alginic acid or combinations thereof; a lubricant, such as magnesium stearate; a sweetening agent, such as sucrose, lactose, saccharin or combinations thereof; a flavoring agent, such as peppermint, oil of wintergreen, cherry flavoring, orange flavoring, and the like; or combinations thereof. When the dosage unit form is a capsule it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid-dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in an appropriate solvent with various other ingredients as disclose above, as required, followed by filter sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsions, the preferred methods of preparation are vacuum-drying or freeze-drying techniques which yield a powder of the active ingredient, optionally with any additional desired ingredient in solid or liquid form. The liquid medium may be suitably buffered, as appropriate, and the liquid composition is rendered isotonic with sufficient saline or glucose where injection is the mode of administration. The preparation of highly concentrated compositions for direct injection is also contemplated, where the use of DMSO as solvent is envisioned to result in extremely rapid penetration, delivering high concentrations of the active agents to a small area.

The composition is preferably stable under the conditions of manufacture and storage, and is preferably preserved against the contaminating action of microorganisms, such as bacteria and fungi. It will be appreciated that endotoxin contamination is desirably kept minimally at a safe level, for example, less than 0.5 ng/mg protein.

In particular embodiments, prolonged absorption of an injectable composition can be brought about by the use in the compositions of agents delaying absorption, such as aluminum monostearate, gelatin or combinations thereof.

G. Kits

Any of the compositions described herein may be formulated into a kit. In a non-limiting example, a vector (e.g., a herpes virus vector comprising a therapeutic nucleic acid for a vascular or cardiovascular disease or disorder) and optionally an additional agent, may be formulated into a kit. The kits will thus contain, in suitable container means, a vector and, optionally, an additional agent.

The kits may comprise a suitably aliquoted vector and optional additional agent composition, whether labeled or unlabeled, which may be used, e.g., to prepare a standard curve for a detection assay. The components of the kits may be packaged either in aqueous media or in solid form, e.g., lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be contained in a vial. The kits of the present invention also will typically include a means for containing the vector and optional additional agent, and any other reagent containers, in close confinement for commercial sale. Such containers may include injection- or blow-molded plastic containers into which the desired vials are retained.

When the components of the kit are provided in one or more liquid solutions, the liquid solution is an aqueous solution, with a sterile aqueous solution being particularly preferred. The vector and optional additional agent composition may also be formulated into a syringeable composition. In the case of syringeable compositions, the container means may itself be a syringe, pipette, and/or other similar apparatus, from which the formulation may be applied to an area of the body, injected into an animal, or applied to, and/or mixed with, the other components of the kit.

The components of the kit also may be provided as dried powder(s). When reagents and/or components are provided as a dry powder, the powder can be reconstituted by the addition of a suitable solvent or liquid carrier in this case of mixtures. It is envisioned that the solvent may also be provided in another container means.

Irrespective of the number and type of containers, the kits of the invention may also comprise, and be packaged with, an instrument for assisting with the injection/administration of a pharmaceutical composition of the present invention within a tissue, organ or body of an animal. Such an instrument may be a syringe, pipette, forceps, or any medically approved delivery device.

The following examples are included to demonstrate preferred embodiments of the invention. However, those of skill in the art will, in light of the present disclosure, appreciate that many alterations can be made in the specific embodiments which are disclosed herein without departing from the spirit and scope of the invention as claimed.

EXAMPLE 1

Vector Preparation

R3616 and R849

Described herein is the construction of a replication competent, neurovirulence-attenuated (debilitated for growth within the central nervous system), recombinant $\gamma_1 34.5$-deleted HSV-1 virus containing the lacZ gene under the control of the $\gamma_1 34.5$ promoter (HSVlacZ or R849). The following methods and vectors are set forth in U.S. Pat. Nos. 5,238,688 and 6,120,773, both incorporated by reference in their entireties.

Although the HSV vector R3616 exemplifies a growth-debilitated HSV via disruption in a non-essential gene or genes, those of skill in the art will recognize that other non-essential HSV genes may be disrupted (e.g., insertion, substitution or deletion) to obtain a similar growth-debilitated HSV (see Table 1 and 3). Further, those of skill will also recognize that such a disrupted gene may be an essential gene (see Tables 1 and 2).

A recombinant virus R3617, lacking 1 Kbp of DNA in each copy of the $\gamma_1 34.5$ gene, was generated by co-introduction into rabbit skin cells of intact R4002 DNA and the DNA of plasmid pRB3616. In plasmid pRB3616, the sequences containing most of the coding region of a $\gamma_1 34.5$ gene, i.e., those located between the BstEII and StuI sites within the BamHI S fragment of HSV-1 strain F, had been deleted. To generate pRB3616, plasmid pRB143 [Post et al., Proc. Nat'l. Acad. Sci. (USA), 7.,7, 4201 (1980)] was digested with BstEII and StuI, blunt-ended with T4 polymerase, and religated. The progeny of the transformation were plated on 143 tk⁻ (thymidine kinase-) cells overlaid with medium containing BUdR (bromodeoxyaridine) to select for tk⁻ viruses. Because the tk gene is present in both copies of the $\gamma_1 34.5$ gene in R4002, the selected progeny contain deletions in both copies. The selected tk⁻ virus, designated R3617, was analyzed for the presence of the deletion in both copies of the $\gamma_1 34.5$ gene. An intact $\gamma_1 34.5$ gene was not present.

For assays of neurovirulence, the deletion in the native tk⁻ gene of R3617, which traces its origin from HSV-1(F)Δ305, had to be repaired. This was accomplished by co-introduction into rabbit skin cells of intact R3617 DNA and Bam HI Q fragment containing the tk gene (Chou and Roizman, 1994). The virus selected for a tk⁺ phenotype in 143tk⁻ cells was designated R3616 (Chou et al., 1990). The recombinant R849 (HSVlacZ) virus carrying the β-galactosidase reporter cassette in place of the $\gamma_1 34.5$ genes was generated as follows. Rabbit skin cells were transfected with intact R4002 DNA and a plasmid having the BstEII-StuI DNA fragment of the $\gamma_1 34.5$ replaced with a BstEII-StuI fragment containing the coding domain of the β-galactosidase gene. Recombination occurred through the flanking sequences. The progeny of the transfection was selected in 143tk⁻ cells in the presence of BUdR. A clone was purified, tested for the presence of the β-galactosidase open reading frame, and then contransfected with BamHI Q DNA fragments to rescue the thymidine kinase gene. In the R849 (HSVlacZ) recombinant virus, the β-galactosidase coding sequence is fused in frame with the $\gamma_1 34.5$ gene coding for the first 28 amino acids of the gene product. The chimeric gene is expressed from the $\gamma_1 34.5$ promoter. Viral titers were measured in Vero cells. R3616 was deposited under accession number ATCC VR2280 with the American Type Culture Collection, Manassas, Va. on Aug. 14, 1990.

Adeno-Associated Viral Vectors

For controls in comparative experiments, adeno-associated viral (AAV) vectors were created and purified as previously described (Svensson et al., 1999). Briefly, the AAV helper plasmid, pAd14 contains the AAV rep and ap genes cloned into the Xba I site, and the SV40 origin of replication cloned into the BamHI site of pBluescript. The virus was purified by CsCl gradient centrifugation, dialyzed against PBS, and stored in aliquots at –80° C. Viral titer was determined by using a dot blot hybridization assay to determine the number of viral genomes/ml. HeLa cells were infected with the virus and detected by staining with 5-bromo-4-chloro-3-indolyl-beta-D-galactopyranoside (X gal) to reveal 3-galactosidase (lacZ) activity 24 hours after infection.

EXAMPLE 2

Cell Culture and MTT Assay

To determine the appropriate dose for vascular gene transfer, human umbilical vein endothelial cells (HUVECs) were contacted with graded concentrations of HSV-1 for 120 min and viability was assessed using a standard 72 hr MTT assay, as described below.

Human umbilical vein endothelial cells (HUVECs; BioWhittaker/Clonetics) were suspended in complete medium EBM-2 (BioWhittaker #CC3 156) and singlequots of EGM-2 (#CC4176) and grown to 100% confluence in P75 flasks in a 37° C. incubator with humidified 5% $CO_2$ For the passage of cells, all reagent pack contents (HBSS, Trypsin/EDTA, TNS; BioWhittaker CC-5034) were thawed in a 37° C. water bath and exhausted media was removed and discarded. HUVECs were washed with enough HBSS to cover them, trypsin/EDTA was added, and flasks were gently agitated under an inverted microscope. Following loss of adherence of cells, trypsin was inactivated with an equal volume of TNS. The cells were centrifuged at 1200 rpm for 5 min and the pellet was resuspended in complete EBM-2 medium and singlequots of EGM-2.

A modified colorimetric assay based on the selective ability of living cells to reduce the yellow salt MTT (3-[4, 5-dimethylthiozol-2-yl]-2,5 diphenyl tetrazolium bromide; Sigma Chemical Co.) to formazan was used to quantitate HUVEC viability following viral exposure. HUVECs were suspended in media and plated into 96-well flat-bottom microtiter plates at a density of $5 \times 10^3$ per ml in a volume of 0.1 ml. Cells were allowed to incubate overnight and then exposed to HSV R3616 suspended in HEPES-buffered saline (HBS) for 2 hr at 37° C. with humidified 5% $CO_2$. The supernatants were aspirated, and 0.1 ml of complete medium EBM-2 was added to each well. The zero plate was allowed to incubate for 60 min. The supernatant was again aspirated and MTT (5 mg/ml) was added to each well of the zero plate for 4 hr at 37° C. After formation of formazan crystals, the supernatant was aspirated with attention not to disturb the underlying cell layer. The formazan crystals were then dissolved in 0.1 ml DMSO (Sigma) and the absorbance measured at 515 nm using a microplate spectrophotometer (SpectraMax 340 004) interfaced with a personal computer (Apple Macintosh). This process was repeated after 72 hours and relative cell survival was calculated. The experiment was repeated a total of three times.

HUVECs infected with R3616 at an MOI=1 survived over 72 hr at a rate of 92±19%. As expected, a decreasing proportion of cells survived with increasing viral concentrations, with only 4±2% cells surviving at an MOI=50. Subsequent viral doses were chosen after approximation of cell number in whole-tissue volumes with MOIs ranging from 1–2.

EXAMPLE 3

Infection of Human Saphenous Veins in Whole Organ Culture

To test in vitro gene transfer in quiescent vascular tissue, human saphenous veins discarded at the time of operation were infected at 120 mmHg for 10 min with vehicle, HSVlacZ (R849), or an adeno-associated virus control containing the lacZ gene (AAVlacZ).

Segments of saphenous vein were harvested from patients at the time of coronary or peripheral bypass surgery under an approved protocol. No patient had any history of venous disease. Human saphenous vein segments were judged to be of good quality by the operating surgeon with diameters ranging from 3.5 to 5.5 mm. Human saphenous veins were infected and cultured whole.

Segments were gently irrigated with saline to remove any residual debris, and excess adventitia trimmed sharply. Vein segments were cut into rings and placed in separate culture wells with RPMI-1640 media/15% FBS and incubated at 37° C. The vein was divided into adjacent control and experimental segments and separately dually cannulated with 22 gauge catheters at both ends for vector infusion and pressure monitoring (Hewlett-Packard 78534B; Palo Alto, Calif.). Veins were distended with either vehicle (n=4), AAVlacZ $4 \times 10^{11}$ pfu/ml (n=2), or HSVlacZ (R849) $6.5 \times 10^8$ pfu/ml for 10 min at 120 mmHg with limited outflow and low shear stress. The main channel of the vein was then rinsed with saline and the vein cut into rings 0.5 cm in length.

The first ring was fixed immediately in 1.25% glutaraldehyde for 10 min, washed in PBS and incubated overnight at 37° C. with X gal in a dark environment for chromogenic assay. The remaining rings (4–7, depending on the amount of vein available) were each placed in separate culture wells with six ml media (RPMI-1640 with 15% FBS) and incubated at 37° C. Media was changed every two days. Vein segments were removed from the media, fixed, and stained with X gal as above after 3, 5, 10, 14, 20, 28, 32, 34, 40, 48, and 55 days.

All segments exposed to HSVlacZ (R849) expressed β-galactosidase. Expression was not present immediately after exposure in any veins, but after 20 days (e.g., 34 days) all veins showed significant expression in the intima and adventitia and, to a lesser extent, the media. Segments were counterstained with eosin. HSV-mediated transgene expression was not limited to the EC layer, but was present in all cell layers, including a significant amount of expression in the medial layer, which appeared to exceed that observed with adenoviral-mediated infection. The ability of HSV to effectively penetrate the EC layer and infect cells deep within the vein wall was also surprising, as it had not been previously demonstrated. Expression persisted to 55 days, the final time point in this study. This is in stark contrast to adenoviral-mediated gene transfer, which generally dissipates after seven days.

Expression after AAVlacZ exposure was minimal, with saphenous veins exposed to AAVlacZ exhibiting inconsistent staining in the intima and adventitia, which was much less pronounced than with HSVlacZ (R849). Expression was not evident in any vein segment exposed to vehicle only.

Sections were also stained with a rabbit anti-human antibody to von Willebrand Factor (vWF) to examine the presence and integrity of the endothelium by immunohistochemistry. 4 μm sections of paraffin-embedded tissues were mounted on poly-L-lysine coated slides, and deparaffinized by sequential 5 min washes with xylene and decreasing concentrations of ethanol and dH$_2$O. Sections were then incubated in pre-warmed 10 mM EDTA (pH 6.0) for 60 min at 70° C., washed three times with dH$_2$O, and incubated in pre-warmed Proteinase K (20 μg/ml in PBS) for 20 min at 37° C. After blocking with a 10% solution of normal goat serum (Vector, Burlingame, Calif.) in 0.5% casein (Sigma) and PBS, endogenous avidin and biotin were quenched using a blocking kit (Vector). Slides were washed three times with 0.5% casein/0.01% Tween 20 in PBS and incubated overnight at 4° C. with rabbit anti-human vWF (DAKO, Denmark) titered to 0.8 μg/ml in 0.5% casein. Appropriate negative controls (rabbit IgG isotype, DAKO) were also used. Slides were washed three times and incubated with goat-anti-rabbit IgG biotinylated secondary antibody (2 μg/ml in PBS, 0.5% casein and 10% normal human serum) for 25 min at 37° C. Endogenous peroxidase was quenched with 3% H$_2$O$_2$ (20 min at room temperature (RT)), and slides were washed and incubated with Vectastain Standard Elite (ABC) for 25 minutes at RT. Tissues were developed with the Vector DAB kit, and counterstained with a 0.03% solution of light green SF yellowish (Fisher, Hanover Park, Ill.). Sections were dehydrated in alcohol and xylene, mounted with Permount and coverslips, and examined via light microscopy.

Treatment with HSVlacZ (R849) did not appreciably affect the integrity of the EC layer as assessed qualitatively by vWF staining in cultured human veins 34 days after exposure to vehicle or HSVlacZ (R849).

EXAMPLE 4

Infection of Rabbit External Jugular Vein Patches

To demonstrate in vivo gene transfer in proliferating vascular tissue, the external jugular vein of male New Zealand White rabbits was exposed to vehicle, HSVlacZ (R849), or AAVlacZ.

Male New Zealand white rabbits (3.5–4 kg) were anesthetized by intramuscular (1 m) injection with ketamine hydrochloride (40 mg/kg) and xylazine (5 mg/kg) augmented with halothane via endotracheal intubation. Antibiotic prophylaxis was provided with enrofloxacin 10 mg/kg IM daily. Using sterile technique, the external jugular vein was exposed and two branches cannulated with 24-gauge catheters. One cannula was used for irrigation and infection, and the other for intralumenal pressure monitoring. The main channel was infected with either vehicle (n=6), AAVlacZ $4 \times 10^{11}$ pfu/ml (n=2), or HSVlacZ (R849) $4 \times 10^8$ pfu/ml (n=4) for 10 min at 100 mmHg.

Following infection, the vein was irrigated with saline, excised and bivalved. The ipsilateral common carotid artery (CCA) was then exposed through the same incision and the animal systemically anticoagulated with heparin (200 U/kg)

intravenously. The CCA was doubly clamped and a 1.5-cm longitudinal arteriotomy made proximal to the cranial thyroid branch. The arteriotomy was reconstructed with external jugular vein patch angioplasty using running 8-0 polypropylene suture (Davis-Geck TE-145; Manatee, PR) under 4.5×-loupe magnification. Ultrasonic transit-time flow through the graft was measured (Transonics Systems Inc. HT207; Ithaca, N.Y.) and recorded using a digital data acquisition system (Lab Master D.M.A.; Scientific Solutions, Inc., Solon, Ohio). All operations for implantation of external jugular vein patches in rabbits were completed without complication. There was no significant difference in mean blood flow in vehicle-treated vs. viral-infected patches at time of implantation (vehicle 15.0±1.2 vs. viral 18±1.0 ml/min; p=NS). The incision was closed and the animal allowed to recover. Anticoagulation was not reversed.

After four weeks, the vein patches were harvested and assessed for patency and β-galactosidase expression using X gal. The animals were reanesthetized and the vein patches reexposed. Intraarterial pressure and blood flow through the patch were again measured and recorded. All vein patches were patent at the time of harvest at four weeks (n=12).

The vein patch was divided into three sections starting one mm distal to the beginning of the patch and ending one mm proximal to its endpoint. The harvested vessels were fixed in 1.25% glutaraldehyde for 10 min, washed in PBS, and incubated overnight at 37° C. with X gal. Five $\mu$m sections were cut from each of the portions of the patch and stained using eosin, hematoxylin and eosin (H & E) and the Weigert van Gieson. Ten high-power fields (40×) of each tissue section were examined using a microscope (Nikon Microphoto-FX) equipped with a digital camera (Sony PowerHAD 3CCD). Stained cells/nuclei were counted using standard imaging software (ImagePro Plus 3.0.1). The total number of β-galactosidase positive cells was counted in the neointima, media and adventitia located circumferentially about the lumen. The total number of cells was counted on the H & E sections in the neointima, media and adventitia. The average number of positive cells was expressed as a percentage of the total number of cells, reflecting the infection efficiency.

All vein patches that had been exposed to HSVlacZ (R849; n=4) showed significant β-galactosidase expression in all layers of the vein wall at 4 weeks after exposure (i.e., infection), especially within the smooth muscle cells (SMCs) comprising the neointima (48±2% infection efficiency). All slides were counterstained with eosin. The calculated infection efficiencies in the adventitia, media, and neointima were 42±1%, 58±3% and 48±2%, respectively. Interestingly, there was also moderate expression in the arterial segment (the posterior wall of the reconstruction), especially near the margins surrounding the suture artifact. In contrast, patches infected with AAVlacZ showed inconsistent transgene expression, mostly confined to the adventitia. Expression was not evident in the vehicle-exposed patches or in any harvested external jugular veins or CCAs contralateral to an HSVlacZ (R849)-infected vein patch or an AAV-infected vein patch.

EXAMPLE 5

Effects of R849 on Cultured Human Cells

To demonstrate the effect of HSV R849 (HSVlacZ) in cultured human cells, human umbilical vein endothelial cells (HUVECs; BioWhittaker/Clonetics #CC2517) and umbilical artery smooth muscle cells (#CC2579) were separately suspended in complete medium EGM bullet kit (#CC3182) and grown to 100% confluence in P75 flasks in a 37° C. incubator with humidified 5% $CO_2$. A modified colorimetric assay based on the selective ability of living cells to reduce the yellow salt MTT (3-[4,5-dimethylthiozol-2-yl]-2,5 diphenyl tetrazolium bromide; Sigma Chemical Co.) to formazan was used to quantitate HUVEC and UASMC viability following viral exposure and rescue with Acyclovir (Abbott Laboratories).

HUVECs infected with R849 (HSVlacZ) at an MOI=1 had relative cell survivals of 102±10% and 81±4% cells after 48 ad 72 hr, respectively. Similarly infected UASMCs had relative cell survivals of 92±10% and 73±6%, respectively. As expected, a decreasing proportion of cells survived with increasing viral concentrations, with only 12±3% of HUVECs and 5±10% of UASMCs surviving after infection with an MOI=25 (relative 72 hr cell survival with Acyclovir (0.25 $\mu$g/ml) was 45±5%; with Acyclovir (0.5 $\mu$g/ml) was 85±9%) while similarly infected UASMCs could not be rescued, even with 10 $\mu$g/ml Acyclovir. These results demonstrate that (1) R849 (HSVlacZ) is relatively non-toxic at low doses, (2) R849 (HSVlacZ) is more toxic to SMCs than endothelical cells (ECs) at higher doses, and (3) a majority of ECs exposed to an MOI=25 can be rescued with therapeutic doses of Acyclovir, while SMCs cannot. Thus, R849 (HSVlacZ) exhibits selectivity for SMCs, the target cell population in this therapeutic strategy.

EXAMPLE 6

Effects of R849 on Whole Human Veins

Effects of R849 (HSVlacZ) on whole human veins were again studied (as described above in Example 3). Unused portions of saphenous veins harvested at the time of coronary or peripheral bypass were cannulated with 22 gauge catheters at both ends and distended for 10 min at 120 mmHg with either vehicle or $1 \times 10^9$ PFU/ml R849 (HSVlacZ; n=8). The first ring was fixed immediately in 1.25% glutaraldehyde for 10 min, washed in PBS, and incubated overnight at 37° C. with X gal in a dark environment. The remaining rings were each placed in separate culture wells with 6 ml media (RPMI-1640 with 30% FBS) and incubated at 37° C. Vein segments were removed from media, fixed, and stained with X gal after 2–55 days.

The results showed that R849 (HSVpacZ)-infected segments exhibited β-galactosidase expression up to 55 days following infection. Interestingly, transgene expression was not limited to the ECs but was present in all cell layers, including a significant amount of expression in the media, which appeared to exceed that observed with adenoviral-mediated infection.

Obviously, any strategy designed to limit restenosis must not disturb the antithrombotic endothelial layer. To test for possible negative effects of HSV on the endothelium, cultured human saphenous veins were exposed to R849 (HSVlacZ) and then examined for the endothelial marker, von Willebrand factor (vWF), by immunostaining. Veins were distended with either vehicle or R849 (HSVlacZ; $6.5 \times 10^8$ pfu/ml) for 10 min at 120 mmHg, as described above. Vein segments were removed from the media, fixed, and stained. Four $\mu$m sections of paraffin-embedded tissues were mounted on poly-L-lysine coated slides, and deparaffinized by sequential 5 min washes with xylene and decreasing concentrations of ethanol and dH20. Slides were washed three times with 0.5% casein/0.01% Tween 20 in PBS and incubated overnight at 4° C. with rabbit anti-human vWF (DAKO, Denmark) titered to 0.8 µg/ml in 0.5% casein. Appropriate negative controls (rabbit lgG isotype, DAKO) were also used. Slides were washed three times and incubated with goat anti-rabbit lgG biotinylated secondary antibody (2 µg/ml in PBS, 0.5% casein and 10% normal human serum) for 25 min at 37° C. Tissues were developed with the Vector DA kit, and counterstained with a 0.03% solution of light green SF yellowish (Fisher, Hanover Park, Ill.). Gene transfer was consistently demonstrated throughout the vascular wall, with the endothelium remaining largely intact as judged by the presence of vWF.

EXAMPLE 7

R849 Infection in Vein Grafts in Immunocompetent Animals

Experiments in the rabbit vein patch model were again performed (as described in Example 4) in order to examine the time course of R849 (HSVlacZ)-mediated infection, with the potential for long-term programmed expression.

Male New Zealand White rabbits (3.5–4 kg) were anesthetized and the external jugular vein was surgically exposed. The main channel was infected with either vehicle (n=6), R849 (HSVlacZ) $4 \times 10^8$ pfu/ml (n=8) or R3616 $3 \times 10^8$ pfu/ml (control virus, n=2) for 10 min at 120 mmHg. Following infection, the vein was excised and fashioned as a common carotid vein patch angioplasty using running 8-0 polypropylene suture. This vein patch technique has the advantage of creating an arterialized vein segment with minimal surgical trauma. After four weeks, the animals were reanesthetized and the vein patches re-exposed. There was no significant difference in mean blood flow in control ($31 \pm 2$ ml/min) vs. viral-infected patches ($34 \pm 3$ ml/min) at the time of implantation. All vein patches were patent at the time of harvest at four weeks. Patches exposed to R849 (HSVlacZ) $4 \times 10^8$ pfu/ml showed marked β-galactosidase staining in all parts of the vessel wall, most notably within the medial layer. Calculated infection efficiencies (percent of cells infected) were $42 \pm 2\%$ in the adventitia, $44 \pm 9\%$ in the media, and $45 \pm 6\%$ in the neointima. Moderate β-galactosidase staining was also detected in the untreated arterial segment adjacent to the vein patch, and in the more distal portions of the native carotid artery. These consistent rates of infection, coupled to stable and durable transgene expression, far exceed the reported results with other vectors.[Moawad et al., *Ann. Vasc. Surg.* 15:367–73, 2001; Schwartz et al., *J. Vasc. Surg.* 29:874–83, 1999; Hanna et al., *J. Vasc. Surg.* 31:770–80, 2000; George et al., *Circ.* 101:296–304, 2000; Eslaim et al., *J. Vasc. Surg.* 31:1149–59, 2000; Dollery et al., *Circ.* 99:3199–205, 1999; Scheinman et al., *J. Vasc. Surg.* 29:360–9, 1999; Schneider et al., *J. Vasc. Surg.* 29:543–50, 1999, and Waugh et al., *Circ.* 102:332–7, 2000]. Furthermore, the dose of R849 (HSVlacZ) required to achieve these results, no greated than $10^8$ pfu/ml, is several orders of magnitude less than traditional strategies using adenovirus (see above).

EXAMPLE 8

Effect of R849 on Neointimal Hyperplasia in Immunocompetent Animals

A novel model of hemodynamically compromised vein patch angioplasty was used to test the effects of R849 (HSVlacZ) on SMC proliferation and neointimal hyperplasia. Compromise of blood flow, with its attendant reductions in shear stress, is a well-known stimulator of SMC proliferation [Rectenwald et al., *Circ.* 102, 2000 and Kumar et al., *Arterioscler Thromb. Vasc. Biol.* 17:2238–44, 1997], and is an important predisposing factor to vein graft failure [Meyerson et al. *J. Vasc. Surg.* 34:90–7, 2001]. Therefore, a model of venous transplantation under profoundly reduced flow was developed in order to simulate failing bypass grafts.

Generally, rabbits underwent surgical vein exposure, R849 (HSVlacZ) infection, and vein patch angioplasty as described in the preceding examples. Prior to wound closure, the main branch of the angioplasty reconstruction (the common carotid artery) was ligated, leaving the only outflow via a small cranial thyroid artery. This had the reproducible effect of decreasing blood flow to approximately 5% o baseline values, a condition that persisted to sacrifice.

The resultant vein patch was grossly thickened and contracted, the thickest ever reported for an animal model of vein grafting. The histological characteristics were similar to those of failing human bypass grafts, including the presence of laminar thrombus and flow-limiting lumenal stenosis.

Specifically, this model was used to test the effects of R849 (HSVlacZ) on SMC proliferation in vivo. Rabbit external jugular veins were infected with either R849 (HSVlacZ; n=8) or vehicle (PBSS; n=6) for 10 min and then fashioned as carotid vein patches with limited outflow. Mean blood flow and shear stress at the time of implantation were similar in R849 (HSVlacZ)-infected ($2.8 \pm 0.3$ ml/min, $0.17 \pm 0.03$ dyne/cm$^2$) and vehicle ($2.6 \pm 1.7$ ml/min, $0.32 \pm 0.1$ dyne/cm$^2$) groups. After four weeks, the vein patches were re-exposed, perfusion-fixed at the last recorded blood pressure, and morphometrically examined for neointimal hyperplasia. Five µm sections were cut, stained using the Weigert van Gieson technique to highlight the internal elastic lamina, and analyzed using digital planimetry (Adobe Photoshop; Adobe Systems, Inc,; San Jose, Calif.). R849 (HSVlacZ)-infected patches were widely patent, with significantly less neointimal hyperplasia than vehicle-treated controls (R849 (HSVlacZ) $280 \pm 28$ vs. vehicle $410 \pm 38$ µm, p=0.003). Treatment with R849 (HSVlacZ) essentially returned the "low-flow" patch morphology to "high-flow" physiology.

EXAMPLE 9

Eradication of Established R849 Infection with Acyclovir and Systemic Toxicity of R849 Infection of R849

The ability to attenuate or eliminate infection after completion of the desired biological effect of the vector would be a significant enhancement to gene therapy strategies, and would serve to limit toxicity and the potential for long-term sequelae. Acyclovir sodium (12-amino-1,9-dihydro-9-[(2-hydroxy-ethoxy)methyl]-6H-purin-6-one; trade name Zovirax; Alphaparm USPD, Inc.) is a synthetic purine nucleoside analog with an antiviral spectrum limited to herpes viruses including herpes simplex, herpes zoster (shingles), varicella (chicken pox), Epstein-Barr virus, and cytomegalovirus. Clinically, its use is limited to the treatment of herpes simplex, genitalis, and zoster infections.

Its mechanism of action is believed to include penetration intracellularly, conversion initially to the monophosphate by viral thymidine kinases, then to the diphosphate by cellular guanylate kinase and, finally, to the triphosphate by various other cellular enzymes. Fully active Acyclovir triphosphate competes with the natural substrate, deoxyguanosine triphosphate, for a position in the DNA chain of the herpes virus. Once incorporated, it terminates DNA synthesis via (1) competitive inhibition of viral DNA polymerase, (2) incorporation into, and termination of, the growing viral DNA chain, and (3) inactivation of the viral DNA polymerase. Uninfected cells show only minimal uptake and phosphorylation of Acyclovir. The HSV strains used in this example retain tk activity and are thus highly susceptible to neutralization by Acyclovir. To test whether an established HSV-1 infection could be eradicated after completion of the desired therapeutic effect (of the recombinant HSV) in vivo, a rabbit model was used. Following surgical exposure, the external jugular vein was infected with R849 (HSVlacZ) at $4 \times 10^8$ pfu/ml (n=8; 0.2–4.0 ml) for 10 min at 120 mmHg and then fashioned as a vein patch atop the common carotid artery as previously described (vein patch angioplasty). Following one week of recovery, half the rabbits (n=4) received Acyclovir (Abbott Laboratories) 75 mg/kg body weight intravenously for a total of five days. Starting on the same post-operative day, rabbits were simultaneously treated with oral Acyclovir (Alphaparm USPD Inc.; 3 mg/cc $H_2O$), which was maintained until sacrifice. Baseline serum Acyclovir, electrolyte, blood urea nitrogen, and creatinine levels were measured before initiation of Acyclovir treatment, on days 2, 5, and 10 after initiation of treatment, and at sacrifice. During Acyclovir therapy, serum levels of Acyclovir were maintained within the therapeutic range (9±4 µg/ml). There was no significant systemic toxicity as measured by serum electrolytes, blood urea nitrogen, and creatinine levels throughout the study. After four weeks, the animals were reanesthetized and the vein patches re-exposed and harvested. Vessels were fixed in 1.25% glutaraldehyde for 10 min, washed in PBS, and incubated overnight at 37° C. with X gal. 5 µm sections were cut and counterstained with eosin. Examination of the sections revealed that Acyclovir treatment completely eliminated reporter gene (lacZ) expression, with β-galactosidase activity evident in <1% of cells (p<0.55). The therapeutic antiproliferative effect appears to be preserved in that treated vein patches remained widely patent even after the R849 (HSVlacZ) infection had been eradicated.

There were no significant aberrations in blood counts, platelet function, coagulation, hepatic or renal function with HSV infection (see Table 6). The infection was localized to the doubly clamped vein so systemic exposure was likely minimal.

Although the present invention has been described in terms of preferred embodiments, it is intended that the present invention encompass all modifications and variations that occur to those skilled in the art upon consideration of the disclosure herein, and in particular those embodiments that are within the broadest proper interpretation of the claims and their requirements. All literature cited herein (scientific articles, U.S. patents, foreign patents, and published patent applications) is incorporated by reference.

TABLE 6

|  | WBC | HEMOGLOBIN | PLATELETS |
|---|---|---|---|
| HSV-infected |  |  |  |
| Day 0 (n = 3) | 4.8, 10.6, 6.5 | 12.0, 11.1, 13.4 | 209, 90, 309 |
| Day 1 (n = 2) | 10.6, 9.3 | 10.2, 9.4 | 115, 260 |
| Day 7 (n = 2) | 7.4, 12.9 | 8.7, 10.7 | 220, 209 |
| Day 14 (n = 1) | 3.5 | 11.1 | 313 |

TABLE 6-continued

|  | WBC | HEMOGLOBIN | PLATELETS |
|---|---|---|---|
| Vehicle-infected |  |  |  |
| Day 0 (n = 1) | 8.7 | 11.6 | 41 |
| Day 1 (n = 1) | 9.5 | 7.3 | 136 |
| Day 7 (n = 1) | 9.0 | 9.7 | 134 |
| Day 14 (n = 1) | 9.4 | 10 | 188 |

|  | PT | PTT |  |
|---|---|---|---|
| HSV-infected |  |  |  |
| Day 0 (n = 3) | 8.1, 5.9, 6.9 | 18.9, 23.4 (one clumped) |  |
| Day 1 (n = 2) | 5.9, 6.4 | 6.9, 20.2 |  |
| Day 7 (n = 2) | 6.4, 5.6 | 12.9, 12.9 |  |
| Day 14 (n = 1) | 6.4 | 19.7 |  |
| Vehicle-infected |  |  |  |
| Day 0 (n = 1) | 7.0 | 21.2 |  |
| Day 1 (n = 1) | 6.2 | 18.6 |  |
| Day 7 (n = 1) | 6.0 | 12.9 |  |
| Day 14 (n = 1) | 6.4 | 19.7 |  |

|  | Tbili | SGOT | SGPT |
|---|---|---|---|
| HSV-infected |  |  |  |
| Day 0 (n = 4) | 0.3, 0.2, 0.2, 0.1 | 94, 23, 10, 11 | 42, 14, 41, 3 |
| Day 1 (n = 2) | 0.2, 0.2 | 72, 104 | 85, 71 |
| Day 7 (n = 2) | 0.3, 0.2 | 12 | 48 |
| Day 14 (n = 1) | 0.0 | 9 | 24 |
| Vehicle-infected |  |  |  |
| Day 0 (n = 1) | 0.2 | 11 | 31 |
| Day 1 (n = 1) | 0.2 | 95 | 60 |
| Day 7 (n = 1) | 0.3 | 14 | 30 |
| Day 14 (n = 1) | 0.2 | 11 | 23 |

|  | BUN | CREATININE |  |
|---|---|---|---|
| HSV-infected |  |  |  |
| Day 0 (n = 4) | 16, 18, 19, 23 | 1.7, 1.6, 1.3, 1.9 |  |
| Day 1 (n = 2) | 13, 30 | 1.4, 1.7 |  |
| Day 7 (n= 1) | 15 | 1.2 |  |
| Day 14 (n = 1) | 24 | 1.3 |  |
| Vehicle-infected |  |  |  |
| Day 0 (n = 1) | 13 | 1.6 |  |
| Day 1 (n = 1) | 21 | 0.0 |  |
| Day 7 (n = 1) | 16 | 1.5 |  |
| Day 14 (n = 1) | 15 | 1.4 |  |

References

The following references, to the extent that they provide exemplary procedural or other details supplementary to those set forth herein, are specifically incorporated herein by reference.

Advani, Sibley, Song, Hallahan, Kataoka, Roizman, Weichselbaum, Enhancement of replication of genetically engineered herpes simplex viruses by ionizing radiation: a new paradigm for destruction of therapeutically intractable tumors,: Gene Ther, 5:160–165, 1998.

Alber, Powell, Vallance, Goodwin, Grahame-Clarke, "Herpesvirus infection accelerates atherosclerosis in the apolipoprotein E-deficient mouse," Circ, 102:779–785, 2000.

Andreansky, Soroceanu, Flotte, Chou, Markert, Gillespie, Roizman, Whitley, "Evaluation of genetically engineered herpes simplex viruses as oncolytic agents for human malignant brain tumors," Can Res, 57:1502–1509, 1997.

Angel, Bauman, Stein, Dellus, Rahmsdorf, and Herrlich, "12-0-tetradecanoyl-phorbol-13-acetate Induction of the Human Collagenase Gene is Mediated by an Inducible Enhancer Element Located in the 5' Flanking Region," Mol. Cell. Biol., 7:2256, 1987a.

Angel, Bauman, Stein, Dellus, Rahmsdorf, and Herrlich, "12-0-tetradecanoyl-phorbol-13-acetate induction of the human collagenase gene is mediated by an inducible enhancer element located in the 5' flanking region," Mol. Cell. Biol., 7:2256, 1987a.

Angel, Imagawa, Chiu, Stein, Imbra, Rahmsdorf, Jonat, Herrlich, and Karin, "Phorbol Ester-Inducible Genes Contain a Common cis Element Recognized by a TPA-Modulated Trans-acting Factor," Cell, 49:729, 1987b Angel, Imagawa, Chiu, Stein, Imbra, Rahmsdorf, Jonat, Herrlich, and Karin, "phorbol ester-inducible genes contain a common cis element recognized by a TPA-modulated trans-acting factor," Cell, 49:729, 1987b Armeanu, Pelisek, Krausz, Fuchs, Groth, Curth, Keil, Quilici, Rolland, Reszka, Nikol, "Optimization of nonviral gene transfer of vascular smooth muscle cells in vitro and in vivo, Molec Ther, 1:366–375, 2000.

Ascher, Scheinman, Hingorani, Seth, Marella, Jacob, "Effect of p53 gene therapy combined with CTLA4Ig selective immunosuppression on prolonged neointima formation reduction in a rat model," Ann Vasc Surg, 14:385–392, 2000.

Atchison and Perry, "Tandem Kappa Immunoglobulin Promoters are Equally Active in the Presence of the Kappa Enhancer: Implications for Model of Enhancer Function," Cell, 46:253, 1986.

Atchison and Perry, "The role of the kappa enhancer and its binding factor nf-kappa b in the developmental regulation of kappa gene transcription," Cell, 48:121, 1987.

Banerji et al., "Expression of a Beta-Globin Gene is Enhanced by Remote SV40 DNA Sequences," Cell, 27:299, 1981.

Banerji, Olson, and Schaffner, "A lymphocyte-specific cellular enhancer is located downstream of the joining region in immunoglobulin heavy-chain genes," Cell, 35:729, 1983.

Baumgartner, Pieczek, Manor, Blair, Kearney, Walsh, Isner, "Constitutive expression of phVEGF165 after intramuscular gene transfer promotes collateral vessel development in patients with critical limb ischemia," Circ, 97:1114–1123, 1998.

Berkhout, Silverman, and Jeang, "Tat Trans-activates the Human Immunodeficiency Virus Through a Nascent RNA Target," Cell, 59:273, 1989.

Bishop, Wiegman, McNamara, Din, Sanders, Hesselbacher et al., "Local adenovirus-mediated delivery of hirudin in a rabbit arterial injury model," J Vasc Res, 36:343–352, 1999.

Blanar, Baldwin, Flavell, and Sharp, "A gamma-interferon-induced factor that binds the interferon response sequence of the MHC class I gene, H-2Kb," EMBO J., 8:1139, 1989.

Bodine and Ley, "An enhancer element lies 3' to the human a gamma globin gene," EMBO J., 6:2997, 1987.

Boshart, Weber, Jahn, Dorsch-Hasler, Fleckenstein, and Schaffner, "A very strong enhancer is located upstream of an immediate early gene of human cytomegalovirus," Cell, 41:521, 1985.

Bosze, Thiesen, and Charnay, "A transcriptional enhancer with specificity for erythroid cells is located in the long terminal repeat of the friend murine leukemia virus," EMBO J., 5:1615, 1986.

Braddock, Chambers, Wilson, Esnouf, Adams, Kingsman, and Kingsman, "HIV-I Tat activates presynthesized RNA in the nucleus," Cell, 58:269, 1989.

Bulla and Siddiqui, "The hepatitis B virus enhancer modulates transcription of the hepatitis B virus surface-antigen gene from an internal location," J. Virol., 62:1437, 1986.

Cable, Caccitolo, Caplice, O'Brien, Simari, Daly, Dearani, Mullany, Orszulak, Schaff, "The role of gene therapy for intimal hyperplasia of bypass grafts," Circ, 100(suppl II):II392-II6, 1999.

Campbell and Villarreal, "Functional analysis of the individual enhancer core sequences of polyoma virus: cell-specific uncoupling of DNA replication from transcription," Mol. Cell. Biol., 8:1993, 1988.

Campere and Tilghman, "Postnatal repression of the alpha-fetoprotein gene is enhancer independent," Genes and Dev., 3:537, 1989.

Campo, Spandidos, Lang, Wilkie, "Transcriptional control signals in the genome of bovine papilloma virus type 1," Nature, 303:77, 1983.

Carbonelli et al. "A plasmid vector for isolation of strong promoters in E. coli," FEMS Microbiol Lett. 177(1):75–82, 1999.

Celander and Haseltine, "Glucocorticoid Regulation of Murine Leukemia Virus Transcription Elements is Specified by Determinants Within the Viral Enhancer Region," J. Virology, 61:269, 1987.

Celander, Hsu, and Haseltine, "Regulatory Elements Within the Murine Leukemia Virus Enhancer Regions Mediate Glucocorticoid Responsiveness," J. Virology, 62:1314, 1988.

Chambers, Gillespic, Soroceanu, Andreansky, Chatterjee, Chou, Roizman, Whitley, "Comparison of genetically engineered herpes simplex virus for the treatment of brain tumors in SCID mouse model of human glioma," PNAS, 92:1411–1415, 1995.

Chandler et al., "RNA splicing specificity determined by the coordinated action of RNA recognition motifs in SR proteins," Proc Natl Acad Sci USA. 94(8):3596–3601, 1997.

Chandler, Maler, and Yamamoto, "DNA sequences bound specifically by glucocorticoid receptor in vitro render a heterlogous promoter hormone responsive in vivo," Cell, 33:489, 1983.

Chang, Barr, Lu, Barton, Leiden, "Adenovirus-mediated over-expression of the cyclin/cyclin-dependent kinase inhibitor, p21 inhibits vascular smooth muscle cell proliferation and neointima formation in the rat carotid artery model of balloon angioplasty," J Clin Invest, 95:2260–2268, 1995.

Chang, Barr, Seltzer, Jiang, Nabel, Nabel, Parmacek, Leiden, "Cytostatic gene therapy for vascular proliferative disorders with a constitutively active form of the retinoblastoma gene product," Science, 267:518–522, 1995.

Chang, Erwin, and Lee, "Glucose-regulated Protein (GRP94 and GRP78) Genes Share Common Regulatory Domains and are Coordinately Regulated by Common Trans-acting Factors," Mol. Cell. Biol., 9:2153, 1989.

Chatterjee, Lee, Rentoumis, and Jameson, "Negative regulation of the thyroid-stimulating hormone alpha gene by thyroid hormone: receptor interaction adjacent to the TATA Box," Proc Natl. Acad Sci. U.S.A., 86:9114, 1989.

Chen and Okayama, "High-efficiency transformation of mammalian cells by plasmid DNA," Mol. Cell. Biol. 7:2745–2752, 1987

Cheng, Mantile, Pauly, Nater, Felici, Monticone, Bilato, Gluzband, Crow, Stetler-Stevenson, Capogrossi, "Adenovirus-mediated gene transfer of the human tissue inhibitor of metalloproteinase-2 blocks vascular smooth muscle cell invasiveness in vitro and modulates neointimal development in vivo," Circ, 98:2195–2201, 1998.

Choi, Chen, Kriegler, and Roninson, "An altered pattern of cross-resistance in multi-drug-resistant human cells results from spontaneous mutations in the mdr-1 (p-glycoprotein) gene," Cell, 53:519, 1988.

Chou and Roizman, "Herpes simplex virus 1 gamma-1 34.5 gene function, which blocks the host response to infection, maps in the homologous domain of the genes expressed during growth arrest and DNA damage," Proc Natl Acad Sci, 91:5247–5251, 1994.

Chou, Kern, Whitley, Roizman, "Mapping of herpes simplex virus-1 neurovirulence to gamma$_1$34.5, a gene nonessential for growth in culture," Science, 250:1261–1266, 1990.

Cocea, "Duplication of a region in the multiple cloning site of a plasmid vector to enhance cloning-mediated addition of restriction sites to a DNA fragment," Biotechniques, 23:814–816, 1997.

Cohen, Walter, and Levinson, "A Repetitive Sequence Element 3' of the Human c-Ha-ras1 Gene Has Enhancer Activity," J. Cell. Physiol., 5:75, 1987.

Costa, Lai, Grayson, and Darnell, "The Cell-Specific Enhancer of the Mouse Transthyretin (Prealbumin) Gene Binds a Common Factor at One Site and a Liver-Specific Factor(s) at Two Other Sites," Mol. Cell. Biol., 8:81, 1988.

Cripe, Haugen, Turk, Tabatabai, Schmid, Durst, Gissmann, Roman, and Turek, "Transcriptional Regulation of the Human Papilloma Virus-16 E6-E7 Promoter by a Keratinocyte-Dependent Enhancer, and by Viral E2 Trans-Activator and Repressor Gene Products: Implications for Cervical Carcinogenesis," EMBO J., 6:3745, 1987.

Culotta and Hamer, "Fine Mapping of a Mouse Metallothionein Gene Metal-Response Element," Mol. Cell. Biol., 9:1376, 1989.

Culver, "Methods for gene transfer and repair. In: Gene therapy: A primer for physicians Culver (ed.), Larchmont, N.Y.: Mary Ann Liebert, Inc., 3–45, 1996.

Dandolo, Blangy, and Kamen, "Regulation of Polyma Virus Transcription in Murine Embryonal Carcinoma Cells," J. Virology, 47:55, 1983.

De Villiers, Schaffner, Tyndall, Lupton, and Kamen, "Polyoma Virus DNA Replication Requires an Enhancer," Nature, 312:242, 1984.

Deschamps, Meijlink, and Verma, "Identification of a Transcriptional Enhancer Element Upstream From the Proto-Oncogene Fos," Science, 230:1174, 1985.

Dollery, Humphries, McClelland, Latchman, McEwan, "Expression of tissue inhibitor of matrix metalloproteinases 1 by use of an adenoviral vector inhibits smooth muscle cell migration and reduces neointima hyperplasia in the rat model of vascular balloon injury," Circ, 99:3199–3205, 1999.

Dunn, Newman, Jones, Yamada, Shayani, Virmani, Dichek, "Seeding of vascular grafts with genetically modified endothelial cells: Secretion of recombinant tPA results in decreased seeded cell retention in vitro and in vivo," Circ, 1439–1446, 1996.

Edbrooke, Burt, Cheshire, and Woo, "Identification of cis-acting sequences responsible for phorbol ester induction of human serum amyloid a gene expression via a nuclear-factor-kappa β-like transcription factor," Mol. Cell. Biol., 9:1908, 1989.

Edlund, Walker, Barr, and Rutter, "Cell-specific expression of the rat insulin gene: evidence for role of two distinct 5' flanking elements," Science, 230:912, 1985.

EPO 0273085

Eslami, Gangadharan, Sui, Rhynhart, Snyder, Conte, "Gene delivery to in situ veins: Differential effects of adenovirus and adeno-associated viral vectors," J Vasc Surg, 31:1149–1159, 2000.

Faries, Pomposelli, Quist, LoGerfo, "Assessing the role of gene therapy in the treatment of vascular disease," Ann Vasc Surg, 14:181–188, 2000.

Fechheirner, Boylan, Parker, Sisken, Patel and Zimmer, "Transfection of mammalian cells with plasmid DNA by scrape loading and sonication loading," Proc Nat'l. Acad. Sci. USA 84:8463–8467, 1987

Feng and Holland, "HIV-I Tat Trans-Activation Requires the Loop Sequence Within Tar," Nature, 334:6178, 1988.

Firak and Subramanian, "Minimal Transcription Enhancer of Simian Virus 40 is a 74-Base-Pair Sequence that Has Interacting Domains," Mol. Cell. Biol., 6:3667, 1986.

Foecking and Hofstetter, "Powerful and Versatile Enhancer-Promoter Unit for Mammalian Expression Vectors," Gene, 45(1):101–105, 1986.

Fortunato, Mauceri, Kocharyan, Song, Salloum, Vosicky et al., "Gene therapy enhances the antiproliferative effect of radiation in intimal hyperplasia," J Surg Res, 89:155–162, 2000.

Fraley, Fomari, Kaplan, "Entrapment of a bacterial plasmid in phospholipid vesicles:potential for gene transfer," Proc Nat'l. Acad. Sci. USA 76:3348–3352, 1979

Fujita, Shibuya, Hotta, Yamanishi, and Taniguchi, "Interferon-Beta Gene Regulation: Tandemly Repeated Sequences of a Synthetic 6-bp Oligomer Function as a Virus-Inducible Enhancer," Cell, 49:357, 1987.

Fulton, Davies, Barber, Svendsen, Hagen, "Locally applied antisense oligonucleotide to proliferating cell nuclear antigen inhibits intimal thickening in experimental vein grafts," Ann Vasc Surg, 12:412–417, 1998.

Fulton, Davies, Koch, Dalen, Svendsen, Hagen, "Antisense oligonucleotide to proto-oncogene c-myb inhibits the formation of intimal hyperplasia in experimental vein grafts," J Vasc Surg, 25:453–463, 1997.

Fulton, Davies, Lefkowitz, Svendsen, Koch, Hagen, "Transfection with βARKCT reduces intimal hyperplasia in experimental vein grafts," Surg Forum, 47:341–345, 1996.

Geary, Clowes, Lau, Vergel, Dale, Osborne, "Gene transfer in baboons using prosthetic vascular grafts seeded with retrovirally transduced smooth muscle cells: A model for local and systemic gene therapy," Human Gene Therapy, 5:1211–1216, 1994.

George, Lloyd, Angelini, Newby, Baker, "Inhibition of late vein graft neointima formation in human and porcine models by adenovirus-mediated overexpression of tissue inhibitor of metalloproteinase-3," Circ, 101:296–304, 2000.

Ghosh and Bachhawat, "Targeting of liposomes to hepatocytes," In: Liver Diseases, Targeted Diagnosis and Therapy Using Specific Receptors and Ligands, Wu and Wu (Eds.), Marcel Dekker, New York, pp 87–104, 1991.

Gilles, Morris, Oi, and Tonegawa, "A tissue-specific transcription enhancer element is located in the major intron of a rearranged immunoglobulin heavy-chain gene," Cell, 33:717, 1983.

Gloss, Bernard, Seedorf, and Klock, "The Upstream Regulatory Region of the Human Papilloma Virus-16 Contains an E2 Protein-Independent Enhancer Which is Specific for Cervical Carcinoma Cells and Regulated by Glucocorticoid Hormones," EMBO J., 6:3735, 1987.

Godbout, Ingram, and Tilghman, "Fine-Structure Mapping of the Three Mouse Alpha-Fetoprotein Gene Enhancers," Mol. Cell. Biol., 8:1169, 1988.

Goodbourn and Maniatis, "Overlapping Positive and Negative Regulatory Domains of the Human β-Interferon Gene," Proc. Natl. Acad. Sci. USA, 85:1447, 1988.

Goodbourn, Burstein, and Maniatis, "The Human Beta-Interferon Gene Enhancer is Under Negative Control," Cell, 45:601, 1986.

Goodman and Gilman's "The Pharmacological Basis of Therapeutics," 8th Ed., 18–32, 43–61, 66–78, 1990.

Graham and Van Der Eb, "A new technique for the assay of infectivity of human adenovirus 5 DNA," Virology 52:456–467, 1973

Greene, Bohnlein, and Ballard, "HIV-1, and Normal T-Cell Growth: Transcriptional Strategies and Surprises," Immunology Today, 10:272, 1989

Grosschedl and Baltimore, "Cell-Type Specificity of Immunoglobulin Gene Expression is Regulated by at Least Three DNA Sequence Elements," Cell, 41:885, 1985.

Hanna, Durán, Leconte, Fox, Neschis, Hobson II, Golden, "Adenoviral-mediated expression of antisense RNA to basic fibroblast growth factor reduces tangential stress in arterialized vein grafts," J Vasc Surg, 31:770–780, 2000.

Hanna, Fox, Neschis, Safford, Swain, Golden, "Antisense basic fibroblast growth factor gene transfer reduces neointimal thickening after arterial injury," J Vasc Surg, 25:320–325, 1997.

Harland and Weintraub, "Translation of mRNA injected into Xenopus oocytes is specifically inhibited by antisense RNA," J. Cell Biol. 101:1094–1099, 1985.

Harrell, Rajanayagam, Doanes, Guzman, Hirschowitz, Crystal, Epstein, Finkel, "Inhibition of vascular smooth muscle cell proliferation and neointimal accumulation by adenovirus-mediated gene transfer of cytosine deaminase," Circ, 96:621–627, 1997.

Haslinger and Karin, "Upstream Promoter Element of the Human Metallothionein-II Gene Can Act Like an Enhancer Element," Proc Natl. Acad. Sci. U.S.A., 82:8572, 1985.

Hauber and Cullen, "Mutational Analysis of the Trans-Activiation-Responsive Region of the Human Immunodeficiency Virus Type I Long Terminal Repeat," J. Virology, 62:673, 1988.

Hensel, Meichle, Pfizenmaier, and Kronke, "PMA-Responsive 5' Flanking Sequences of the Human TNF Gene," Lymphokine Res., 8:347, 1989.

Herr and Clarke, "The SV40 Enhancer is Composed of Multiple Functional Elements That Can Compensate for One Another," Cell, 45:461, 1986.

Hirochika, Browker, and Chow, "Enhancers and Trans-Acting E2 Transcriptional Factors of Papilloma Viruses," J. Virol., 61:2599, 1987.

Hirsch, Gaugler, Deagostini-Bauzin, Bally-Cuif, and Gordis, "Identification of Positive and Negative Regulatory Elements Governing Cell-Type-Specific Expression of the Neural-Cell-Adhesion-Molecule Gene," Mol. Cell. Biol., 10:1959, 1990.

Holbrook, Gulino, and Ruscetti, "cis-Acting Transcriptional Regulatory Sequences in the Gibbon Ape Leukemia Virus (GALV) Long Terminal Repeat," Virology, 157:211, 1987.

Horlick and Benfield, "The Upstream Muscle-Specific Enhancer of the Rat Muscle Creatine Kinase Gene is Composed of Multiple Elements," Mol. Cell. Biol., 9:2396, 1989.

Huang, Ostrowski, Berard, and Hagar, "Glucocorticoid regulation of the ha-musv p21 gene conferred by sequences from mouse mammary tumor virus," Cell, 27:245, 1981.

Huard, Goins, Fink, "Herpes simplex virus type I vector mediated gene transfer to muscle," Gene Ther, 2:385–392, 1995.

Hug, Costas, Staeheli, Aebi, and Weissmann, "Organization of the Murine Mx Gene and Characterization of its Interferon- and Virus-Inducible Promoter," Mol. Cell. Biol., 8:3065, 1988.

Hwang, Lim, and Chae, "Characterization of the S-Phase-Specific Transcription Regulatory Elements in a DNA-Replication-Independent Testis-Specific H2B (TH2B) Histone Gene," Mol. Cell. Biol., 10:585, 1990.

Imagawa, Chiu, and Karin, "Transcription Factor AP-2 Mediates Induction by Two Different Signal-Transduction Pathways: Protein Kinase C and cAMP," Cell, 51:251, 1987.

Imbra and Karin, "Phorbol Ester Induces the Transcriptional Stimulatory Activity of the SV40 Enhancer," Nature, 323:555, 1986.

Imler, Lemaire, Wasvlyk, and Waslyk, "Negative regulation contributes to tissue specificity of the immunoglobulin heavy-chain enhancer," Mol. Cell. Biol, 7:2558, 1987.

Imperiale and Nevins, "Adenovirus 5 E2 Transcription Unit: an E1A-Inducible Promoter with an Essential Element that Functions Independently of Position or Orientation," Mol. Cell. Biol., 4:875, 1984.

Isner, Walsh, Rosenfield, Schainfeld, Asahara, Hogan, Pieczek, "Arterial gene therapy for restenosis," Hum Gene Ther, 7:989–1011, 1996.

Isner, Walsh, Symes, Pieczek, Takeshita, Lowry, Rossow, Rosenfield, Weir, Brogi, Schainfeld, "Arterial gene therapy for therapeutic angiogenesis in patients with peripheral artery disease," Circ, 91:2687–2692, 1995.

Jakobovits, Smith, Jakobovits, and Capon, "A Discrete Element 3' of Human Immunodeficiency Virus 1 (HIV-1) and HIV-2 mRNA Initiation Sites Mediates Transcriptional Activation by an HIV Trans-Activator," Mol. Cell. Biol., 8:2555, 1988.

Jameel and Siddiqui, "The Human Hepatitis B Virus Enhancer Requires Transacting Cellular Factor(s) for Activity," Mol. Cell. Biol., 6:710, 1986.

Jaynes, Johnson, Buskin, Gartside, and Hauschka, "The Muscle Creatine Kinase Gene is Regulated by Multiple Upstream Elements, Including a Muscle-Specific Enhancer," Mol. Cell. Biol., 8:62, 1988.

Johnson, Wold, and Hauschka, "Muscle creatine kinase sequence elements regulating skeletal and cardiac muscle expression in transgenic mice," Mol. Cell. Biol., 9:3393, 1989.

Kadesch and Berg, "Effects of the Position of the Simian Virus 40 Enhancer on Expression of Multiple Transcription Units in a Single Plasmid," Mol. Cell. Biol., 6:2593, 1986.

Kaneda et al., "Increased expression of DNA cointroduced with nuclear protein in adult rat liver," Science, 243:375–378, 1989.

Kaneda et al., "Introduction and expression of the human insulin gene in adult rat liver," J Biol Chem., 264(21):12126–12129, 1989.

Karin, Haslinger, Heguy, Dietlin, and Cooke, "Metal-Responsive Elements Act as Positive Modulators of Human Metallothionein-IIA Enhancer Activity," Mol. Cell. Biol., 7:606, 1987.

Karin, Haslinger, Heguy, Dietlin, and Cooke, "Metal-Responsive Elements Act as Positive Modulators of Human Metallothionein-IIA Enhancer Activity," Mol. Cell. Biol., 7:606, 1987.

Katinka, Vasseur, Montreau, Yaniv, and Blangy, "Polyoma DNA sequences involved in the control of viral gene expression in murine embryonal carcinoma cells," Nature, 290:720, 1981.

Katinka, Yaniv, Vasseur, and Blangy, "Expression of polyoma early functions in mouse embryonal carcinoma cells depends on sequence rearrangements in the beginning of the late region," Cell, 20:393, 1980.

Kato et al., "Expression of hepatitis β virus surface antigen in adult rat liver. Co-introduction of DNA and nuclear protein by a simplified liposome method," J Biol Chem., 266(6):3361–3364, 1991.

Kawamoto, Makino, Niw, Sugiyama, Kimura, Anemura, Nakata, and Kakunaga, "Identification of the Human Beta-Actin Enhancer and its Binding Factor," Mol. Cell. Biol., 8:267, 1988.

Kay, "Adenoviral vectors: Promises and pitfalls," J Vasc Surg, 24:160–161, 1996.

Key, Vercellotti, Winkelmann, Moldow, Goodman, Esmon, Esmon, Jacob, "Infection of vascular endothelial cells with herpes simplex virus enhances tissue factor activity and reduces thrombomodulin expression," Proc Natl Acad Sci, 87:7095–7099, 1990.

Kiledjian, Su, Kadesch, "Identification and characterization of two functional domains within the murine heavy-chain enhancer," Mol. Cell. Biol., 8:145, 1988.

Klamut, Gangopadyhay, Worton, and Ray, "Molecular and Functional Analysis of the Muscle-Specific Promoter Region of the Duchenne Muscular Dystrophy Gene," Mol. Cell. Biol., 10:193, 1990.

Koch, Benoist, and Mathis, "Anatomy of a new β-cell-specific enhancer," Mol. Cell. Biol., 9:303, 1989.

Kotin, "Prospects for the use of adeno-associated virus as a vector for human gene therapy," Hum Gene Ther, 5:793–801, 1994.

Kriegler and Botchan, "A retrovirus LTR contains a new type of eukaryotic regulatory element," In: Eukaryotic Viral Vectors, Gluzman (ed.), Cold Spring Harbor, Cold Spring Harbor Laboratory, NY, 1982.

Kriegler and Botchan, "Enhanced transformation by a simian virus 40 recombinant virus containing a Harvey murine sarcoma virus long terminal repeat," Mol. Cell. Biol. 3:325, 1983.

Kriegler et al., "Promoter substitution and enhancer augmentation increases the penetrance of the sv40 a gene to levels comparable to that of the harvey murine sarcoma virus ras gene in morphologic transformation," In: Gene Expression, Alan Liss (Ed.), Hamer and Rosenberg, New York, 1983.

Kriegler et al., "Viral Integration and Early Gene Expression Both Affect the Efficiency of SV40 Transformation of Murine Cells: Biochemical and Biological Characterization of an SV40 Retrovirus," In: Cancer Cells 2/Oncogenes and Viral Genes, Van de Woude et al. (eds), Cold Spring Harbor, Cold Spring Harbor Laboratory, 1984.

Kriegler, Perez, Defay, Albert and Liu, "A Novel Form of TNF/Cachectin Is a Cell-Surface Cytotoxix Transmembrane Protein: Ramifications for the Complex Physiology of TNF," Cell, 53:45, 1988.

Kriegler, Perez, Hardy and Botchan, "Transformation mediated by the sv40 t antigens: separation of the overlapping sv40 early genes with a retroviral vector," Cell, 38:483, 1984.

Kuhbandner et al., "Temporally controlled somatic mutagenesis in smooth muscle," Genesis 28(1):15–22, 2000.

Kuhl, De La Fuenta, Chaturvedi, Parinool, Ryals, Meyer, and Weissman, "Reversible Silencing of Enhancers by Sequences Derived From the Human IFN-alpha Promoter," Cell, 50:1057, 1987.

Kunz, Zimmerman, Heisig, and Heinrich, "Identification of the Promoter Sequences Involved in the Interleukin-6-Dependent Expression of the Rat Alpha-2-Macroglobulin Gene," Nucl. Acids Res., 17:1121, 1989.

Lachmann and Efstathiou, :The use of herpes simplex virus-based vectors for gene delivery to the nervous system," Molec Med Today, 3:404–411, 1997.

Larsen, Harney, and Moore, "Repression medaites cell-type-specific expression of the rat growth hormone gene," Proc Natl. Acad. Sci. USA., 83:8283, 1986.

Laspia, Rice, and Mathews, "HIV-1 Tat protein increases transcriptional initiation and stabilizes elongation," Cell, 59:283, 1989.

Latimer, Berger, and Baumann, "Highly conserved upstream regions of the alpha. sub. 1-antitrypsin gene in two mouse species govern liver-specific expression by different mechanisms," Mol. Cell. Biol., 10:760, 1990.

Lee, Mulligan, Berg, and Ringold, "Glucocorticoids Regulate Expression of Dihydrofolate Reductase cDNA in Mouse Mammary Tumor Virus Chimaeric Plasmids," Nature, 294:228, 1981.

Levenson et al., "Internal ribosomal entry site-containing retroviral vectors with green fluorescent protein and drug resistance markers," Human Gene Therapy, 9:1233–1236, 1998.

Levinson, Khoury, VanDeWoude, and Gruss, "Activation of SV40 Genome by 72-Base-Pair Tandem Repeats of Moloney Sarcoma Virus," Nature, 295:79, 1982.

Lim, Chapman, Gammon, Muhlestein, Bauman, Stack, Swain, "Direct in vivo gene transfer into the coronary and peripheral vasculatures of the intact dog," Circ, 83:2007–2011, 1991.

Lin, Cross, Halden, Dragos, Toledano, and Leonard, "Delineation of an enhancerlike positive regulatory element in the interleukin-2 receptor alpha.-chain gene," Mol. Cell. Biol., 10:850, 1990.

Luria, Gross, Horowitz, and Givol, "Promoter Enhancer Elements in the Rearranged Alpha-Chain Gene of the Human T-Cell Receptor," EMBO J., 6:3307, 1987.

Lusky and Botchan, "Transient Replication of Bovine Papilloma Virus Type 1 Plasmids: cis and trans Requirements," Proc Natl. Acad. Sci. U.S.A., 83:3609, 1986.

Lusky, Berg, Weiher, and Botchan, "Bovine Papilloma Virus Contains an Activator of Gene Expression at the Distal End of the Early Transcription Unit," Mol. Cell. Biol. 3:1108, 1983.

Lynch, Hara, Leonard, Williams, Dean, Geary, "Adeno-associated virus vectors for vascular gene delivery," Circ Res, 80:497–505, 1997.

Macejak and Sarnow, "Internal initiation of translation mediated by the 5' leader of a cellular mRNA," Nature, 353:90–94, 1991.

Macejak and Sarnow, "Internal initiation of translation mediated by the 5' leader of a cellular mRNA," Nature, 353:90–94, 1991.

Majors and Varmus, "A Small Region of the Mouse Mammary Tumor Virus Long Terminal Repeat Confers Glucocorticoid Hormone Regulation on a Linked Heterologous Gene," Proc. Natl. Acad. Sci. U.S.A., 80:5866, 1983.

Mann, Gibbons, Kernoff, Diet, Tsao, Cooke, Kaneda, Dzau, "Genetic engineering of vein grafts resistant to atherosclerosis," Proc Natl Acad Sci, 92:4502–4506, 1995.

Martuza, Malick, Markert, Ruffner, Coen, "Experimental therapy of human glioma by means of a genetically engineered virus mutant," Science, 252:854–856, 1991.

Matsumoto, Komori, Yonemitsu, Morishita, Sueishi, Kaneda, Sugimachi, "Hemagglutinating virus of Japan-liposome-mediated gene transfer of endothelial cell nitric oxide synthase inhibits intimal hyperplasia of canine vein grafts under conditions of poor runoff," J Vasc Surg, 27:135–144, 1998.

Matsumura, Kim, Shively, MacDonald, Pearce, "Characterization of vascular gene transfer using a novel cationic lipid," J Surg Res, 85:339–345, 1999.

McGovern, Pankow, Shahar, Doliszny, Folsom, Blackburn, Luepker, "Recent trends in acute coronary heart disease—mortality, morbidity, medical care, and risk factors," N Engl J Med, 334:884–890, 1996.

McNeall, Sanchez, Gray, Chesterman, and Sleigh, "Hyper-inducible Gene Expression From a Metallotionein Promoter Containing Additional Metal-Responsive Elements," Gene, 76:81, 1989.

Miksicek, Heber, Schmid, Danesch, Posseckert, Beato, and Schutz, "Glucocorticoid Responsiveness of the Transcriptional Enhancer of Moloney Murine Sarcoma Virus," Cell, 46:203, 1986.

Mineta, Rabkin, Martuza, "Treatment of malignant gliomas using ganciclovir-hypersensitive, ribonucleotide reductase-deficient herpes simplex viral mutant," Cancer Res, 54:3963–3966, 1994.

Miyatake, Yukawa, Toda, Matsuoka, Takahashi, Hashimoto, "Inhibition of rat vascular smooth muscle cell proliferation in vitro and in vivo by recombinant replication-competent herpes simplex virus," Stroke, 30:2431–2438, 1999.

Mordacq and Linzer, "Co-localization of Elements Required for Phorbol Ester Stimulation and Glucocorticoid Repression of Proliferin Gene Expression," Genes and Dev., 3:760, 1989.

Moreau, Hen, Wasylyk, Everett, Gaub, and Chambon, "The SV40 base-repair repeat has a striking effect on gene expression both in sv40 and other chimeric recombinants," Nucl. Acids Res., 9:6047, 1981.

Muesing, Smith, and Capon, "Regulation of mRNA Accumulation by a Human Immunodeficiency Virus Trans-Activator Protein," Cell, 48:691, 1987.

Muzyczka, "Use of adeno-associated virus as a general transduction vector for mammalian cells," Curr Top Microbiol Immunol, 158:97–129, 1992.

Nabel et al., "Recombinant fibroblast growth factor-1 promotes intimal hyperplasia and angiogenesis in arteries in vivo," Nature, 362:844–846, 1993.

Nabel et al., "Recombinant gene expression in vivo within endothelial cells of the arterial wall," Science, 244:1342–1344, 1989.

Neschis, Safford, Hanna, Fox, Golden, "Antisense basic fibroblast growth factor gene transfer reduces early intimal thickening in a rabbit femoral artery balloon injury model," J Vasc Surg, 27:126–134, 1998.

Nicolau and Sene, "Liposome-mediated DNA transfer in eukaryotic cells: dependence of the transfer efficiency upon the type of liposomes used and the host cell cycle stage," Biochem. Biophys. Acta, 721:185–190, 1982.

Nicolau et al., "Liposomes as carriers for in vivo gene transfer and expression," Methods Enzymol., 149:157–176, 1987.

Nicolau, LePape, Soriano, Fargette, Juhel, "In vivo expression of rat insulin after intravenous administration of the liposome-entrapped gene for rat insulin I," Proc Natl Acad Sci, 80:1068–1072, 1983.

Ohno et al., "Gene therapy for the treatment of brain tumors using intra-tumoral transduction with the thymidine kinase gene and intravenous ganciclovir," Hum. Gene Ther. 4:39–69, 1993.

Omitz, Hammer, Davison, Brinster, and Palmiter, "Promoter and enhancer elements from the rat elastase i gene function independently of each other and of heterologous enhancers," Mol. Cell. Biol. 7:3466, 1987.

Ondek, Sheppard, and Herr, "Discrete Elements Within the SV40 Enhancer Region Display Different Cell-Specific Enhancer Activities," EMBO J., 6:1017, 1987.

Palmiter, Chen, and Brinster, "Differential regulation of metallothionein-thymidine kinase fusion genes in transgenic mice and their offspring," Cell, 29:701, 1982.

PCT Application No. WO 94/09699

PCT Application No. WO 95/06128

Pech, Rao, Robbins, and Aaronson, "Functional identification of regulatory elements within the promoter region of platelet-derived growth factor 2," Mol. Cell. Biol., 9:396, 1989.

Pelletier and Sonenberg, "Internal initiation of translation of eukaryotic mRNA directed by a sequence derived from poliovirus RNA," Nature, 334:320–325, 1988.

Perales et al., "Gene transfer in vivo: sustained expression and regulation of genes introduced into the liver by receptor-targeted uptake," Proc. Natl. Acad. Sci. USA, 91:4086–4090, 1994.

Perez-Stable and Constantini, "Roles of fetal γ-globin promoter elements and the adult β-globin 3' enhancer in the stage-specific expression of globin genes," Mol. Cell. Biol., 10:1116, 1990.

Picard and Schaffner, "A Lymphocyte-Specific Enhancer in the Mouse Immunoglobulin Kappa Gene," Nature, 307:83, 1984.

Pinkert, Omitz, Brinster, and Palmiter, "An albumin enhancer located 10 kb upstream functions along with its promoter to direct efficient, liver-specific expression in transgenic mice," Genes and Dev., 1:268, 1987.

Ponta, Kennedy, Skroch, Hynes, and Groner, "Hormonal Response Region in the Mouse Mammary Tumor Virus Long Terminal Repeat Can Be Dissociated From the Proviral Promoter and Has Enhancer Properties," Proc. Natl. Acad. Sci. U.S.A., 82:1020, 1985.

Porton, Zaller, Lieberson, and Eckhardt, "Immunoglobulin heavy-chain enhancer is required to maintain transfected .gamma.2a gene expression in a pre-b-cell line," Mol. Cell. Biol., 10:1076, 1990.

Potter et al., "Enhancer-dependent expression of human k immunoglobulin genes introduced into mouse pre-B lymphocytes by electroporation," Proc Nat'l Acad. Sci. USA, 81:7161–7165, 1984.

Queen and Baltimore, "Immunoglobulin gene transcription is activated by downstream sequence elements," Cell, 35:741, 1983.

Quinn, Farina, Gardner, Krutzsch, and Levens, "Multiple components are required for sequence recognition of the ap1 site in the gibbon ape leukemia virus enhancer," Mol. Cell. Biol., 9:4713, 1989.

Redondo, Hata, Brocklehurst, and Krangel, "A T-Cell-Specific Transcriptional Enhancer Within the Human T-Cell Receptor .delta. Locus," Science, 247:1225, 1990.

Reisman and Rotter, "Induced Expression From the Moloney Murine Leukemia Virus Long Terminal Repeat During Differentiation of Human Myeloid Cells is Mediated Through its Transcriptional Enhancer," Mol. Cell. Biol., 9:3571, 1989.

Remington's Pharmaceutical Sciences, 18th Ed. Mack Printing Company, 1990.

Remington's Pharmaceutical Sciences, 18th Edition, Chapter 61, pages 1289–1329, 1990.

Resendez Jr., Wooden, and Lee, "Identification of highly conserved regulatory domains and protein-binding sites in the promoters of the rat and human genes encoding the stress-inducible 78-kilodalton glucose-regulated protein," Mol. Cell. Biol., 8:4579, 1988.

Riessen, Rahimizadeh, Blessing, Takeshita, Barry, Isner, "Arterial gene transfer using pure DNA applied directly to a hydrogel-coated angioplasty balloon," Hum Gene Ther, 4:749–458, 1993.

Ripe, Lorenzen, Brenner, and Breindl, "Regulatory elements in the 5' flanking region and the first intron contribute to transcriptional control of the mouse alpha-1-type collagen gene," Mol. Cell. Biol., 9:2224, 1989.

Rippe, Brenner and Leffert, "DNA-mediated gene transfer into adult rat hepatocytes in primary culture," Mol. Cell Biol., 10:689–695, 1990.

Rittling, Coutinho, Amarm, and Kolbe, "AP-1/jun-binding Sites Mediate Serum Inducibility of the Human Vimentin Promoter," Nuc. Acids Res., 17:1619, 1989.

Rolling, Nong, Pisvin, Collen, "Adeno-associated virus-mediated gene transfer into rat carotid arteries," Gene Ther, 4:757–761, 1997.

Rosen, Sodroski, and Haseltine, "The location of cis-acting regulatory sequences in the human t-cell lymphotropic virus type III (HTLV-111/LAV) long terminal repeat," Cell, 41:813, 1988.

Rosengart, Lee, Patel, Sanborn, Parikh, Bergman et al., "Angiogenesis gene therapy: phase I assessment of direct intramyocardial administration of an adenovirus vector expressing VEGF121 cDNA to individuals with clinically significant severe coronary artery disease," Circ, 100:468–474, 1999.

Sakai, Helms, Carlstedt-Duke, Gustafsson, Rottman, and Yamamoto, "Hormone-Mediated Repression: A Negative Glucocorticoid-Response Element From the Bovine Prolactin Gene," Genes and Dev., 2:1144, 1988.

Satake, Furukawa, and Ito, "Biological activities of oligonucleotides spanning the f9 point mutation within the enhancer region of polyoma virus DNA," J. Virology, 62:970, 1988.

Schaffner, Schirm, Muller-Baden, Wever, and Schaffner, "Redundancy of Information in Enhancers as a Principle of Mammalian Transcription Control," J. Mol. Biol., 201:81, 1988.

Scheinman, Asher, Levi, Hingorani, Shirazian, Seth, "p53 gene transfer to the injured rat carotid artery decreases neointimal formation," J Vasc Surg, 29:360–369, 1999.

Schneider, Sassani, Vassalli, Driscoll, Dichek, "Adventitial delivery minimizes the proinflammatory effects of adenoviral vectors," J Vasc Surg, 29:543–550, 1999.

Schwartz and Moawad, "Gene therapy for vascular disease," Ann Vasc Surg, 11:189–99, 1997.

Schwartz, Moawad, Svensson, Tufts, Meyerson, Baunoch, Leiden, "Adenoviral-mediated transfer of a constitutively active form of the retinoblastoma gene product attenuates neointimal thickening in experimental vein grafts," J Vasc Surg, 29:874–883, 1999.

Searle, Stuart, and Palmiter, "Building a metal-responsive promoter with synthetic regulatory elements," Mol. Cell. Biol., 5:1480, 1985.

Sharp and Marciniak, "HIV Tar: an RNA Enhancer?," Cell, 59:229, 1989.

Shaul and Ben-Levy, "Multiple Nuclear Proteins in Liver Cells are Bound to Hepatitis B Virus Enhancer Element and its Upstream Sequences," EMBO J., 6:1913, 1987.

Sherman, Basta, Moore, Brown, and Ting, "Class II Box Consensus Sequences in the HLA-DR.alpha. Gene: Transcriptional Function and Interaction with Nuclear Proteins," Mol. Cell. Biol.,9:50, 1989.

Sleigh and Lockett, "SV40 Enhancer Activation During Retinoic-Acid-Induced Differentiation of F9 Embryonal Carcinoma Cells," J. EMBO, 4:3831, 1985.

Smith, Wills, Antelman et. al., "Adenoviral constructs encoding phosphorylation-competent full-length and truncated forms of the human retinoblastoma protein inhibit myocyte proliferation and neointima formation," Circ, 96:1899–1905, 1997.

Spalholz, Yang, and Howley, "Transactivation of a Bovine Papilloma Virus Transcriptional Regulatory Element by the E2 Gene Product," Cell, 42:183, 1985.

Spandau and Lee, "Trans-Activation of Viral Enhancers by the Hepatitis B Virus X Protein," J. Virology, 62:427, 1988.

Spandidos and Wilkie, "Host-Specificities of Papilloma Virus, Moloney Murine Sarcoma Virus and Simian Virus 40 Enhancer Sequences," EMBO J., 2:1193, 1983.

Stephens and Hentschel, "The Bovine Papilloma Virus Genome and its Uses as a Eukaryotic Vector," Biochem. J., 248:1, 1987.

Stuart, Searle, and Palmiter, "Identification of Multiple Metal Regulatory Elements in Mouse Metallothionein-I Promoter by Assaying Synthetic Sequences," Nature, 317:828, 1985.

Sullivan and Peterlin, "Transcriptional Enhancers in the HLA-DQ Subregion," Mol. Cell. Biol., 7:3315, 1987.

Svensson and Schwartz, "Gene therapy for vascular disease," Curr Opin Cardiol, 13:369–374, 1998.

Svensson, Marshall, Woodard, Lin, Jiang, Chu, Leiden, "Efficient and stable transduction of cardiomyocytes after intramyocardial injection or intracoronary perfusion with recombinant adeno-associated virus vectors," Circ, 99:201–205, 1999.

Swartzendruber and Lehman, "Neoplastic Differentiation: Interaction of Simian Virus 40 and Polyoma Virus with Murine Teratocarcinoma Cells," J. Cell. Physiology, 85:179, 1975.

Symes, Losordo, Vale, Lathi, Esakof, Mayskiy, Isner, "Gene therapy with vascular endothelial growth factor for inoperable coronary artery disease," Ann Thor Surg, 68:830–836, 1999.

Takebe, Seiki, Fujisawa, Hoy, Yokota, Arai, Yoshida, and Arai, "SR.alpha. Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," Mol. Cell. Biol., 8:466, 1988.

Takeshita, Gal, Leclerc, Pickering, Riessen, Weir, Isner, "Increased gene expression after liposome-mediated arterial gene transfer associated with intimal smooth muscle cell proliferation," J Clin Invest, 93:652–661, 1994.

Tavernier, Gheysen, Duerinck, Can Der Heyden, and Fiers, "Deletion Mapping of the Inducible Promoter of Human IFN-beta Gene," Nature, 301:634, 1983.

Taylor and Kingston, "E1A Trans-Activation of Human HSP70 Gene Promoter Substitution Mutants is Independent of the Composition of Upstream and TATA Elements," Mol. Cell. Biol., 10:176, 1990.

Taylor and Kingston, "Factor Substitution in a Human HSP70 Gene Promoter: TATA-Dependent and TATA-Independent Interactions," Mol. Cell. Biol., 10:165, 1990.

Taylor, Solomon, Weiner, Paucha, Bradley, and Kingston, "Stimulation of the Human Heat-Shock Protein 70 Promoter in vitro by Simian Virus 40 Large T Antigen," J. Biol. Chem., 264:15160, 1989.

Thiesen, Bosze, Henry, and Charnay, "A DNA Element Responsible for the Different Tissue Specificities of Friend and Moloney Retroviral Enhancers," J. Virology, 62:614, 1988.

Treisman, "Transient Accumulation of c-fos RNA Following Serum Stimulation Requires a Conserved 5' Element and c-fos 3' Sequences," Cell, 42:889, 1985.

Tronche, Rollier, Bach, Weiss, and Yaniv, "The Rat Albumin Promoter: Cooperation with Upstream Elements is Required When Binding of APF/HNF 1 to the Proximal Element is Partially Impaired by Mutation or Bacterial Methylation," Mol. Cell. Biol., 9:4759, 1989.

Trudel and Constantini, "A 3' Enhancer Contributes to the Stage-Specific Expression of the human Beta-Globin Gene," Genes and Dev., 6:954, 1987.

Tur-Kaspa, Teicher, Levine, Skoultchi and Shafritz, "Use of electroporation to introduce biologically active foreign genes into primary rat hepatocytes," Mol. Cell Biol., 6:716–718, 1986.

Turunen, Hiltunen, Ruponen, Virkamaki, Szoka, Jr., Urtti, Ylä-Herttuala, "Efficient adventitial gene delivery to rabbit carotid artery with cationic polymer-plasmid complexes," Gene Ther, 6:6–11, 1999.

Tyndall, La Mantia, Thacker, Favaloro, and Kamen, "A Region of the Polyoma Virus Genome Between the Replication Origin and Late Protein-Coding Sequences is Required in cis for Both Early Gene Expression and Viral DNA Replication," Nuc. Acids. Res., 9:6231, 1981.

U.S. Pat. No. 5,322,783
U.S. Pat. No. 5,384,253
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,935,819
U.S. Pat. No. 5,945,100
U.S. Pat. No. 5,981,274
U.S. Pat. No. 5,994,624

Ueno, Haruno, Morisaki, Furuya, Kangawa, Takeshita, Saito, "Local expression of C-type natriuretic peptide markedly suppresses neointimal formation in rat injured arteries through an autocrine/paracrine loop," Circ, 96:2272–2279, 1997.

Vannice and Levinson, "Properties of the Human Hepatitis B Virus Enhancer: Position Effects and Cell-Type Nonspecificity," J. Virology, 62:1305, 1988.

Varenne, Pislaru, Gillikns, Van Pelt, Gerard, Zoldhelyi, Van de Werf, Collen, Janssens, "Local adenovirus-mediated transfer of human endothelial nitric oxide synthase reduces luminal narrowing after coronary angioplasty in pigs," Circ, 98:919–926, 1998.

Vasseur, Kress, Montreau, and Blangy, "Isolation and characterization of polyoma virus mutants able to develop in multipotential murine embryonal carcinoma cells," Proc Natl. Acad. Sci. U.S.A., 77:1068, 1980.

Wagner et al., Science, 260:1510–1513, 1990.
Wagner et al., Proc. Natl. Acad. Sci. 87(9):3410–3414, 1990.
Wang et al., Biochimica et Biophysica Acta 888(2):225–36, 1986.

Waugh, Li-Hawkins, Yuksel, Kuo, Cifra, Hilfiker et al., "Thrombomodulin overexpression to limit neointima formation," Circ, 02:332–337, 2000.

Weber, De Villiers, and Schaffner, "An SV40 'Enhancer Trap' Incorporates Exogenous Enhancers or Generates Enhancers From its Own Sequences," Cell, 36:983, 1984.

Weinberger, Jat, and Sharp, "Localization of a repressive sequence contributing to b-cell specificity in the immunoglobulin heavy-chain enhancer," Mol. Cell. Biol., 8:988, 1984.

Wilson et al., "Implantation of vascular grafts lined with genetically modified endothelial cells," Science, 244:1344–1346, 1989.

Wilson et al., "Implantation of vascular grafts lined with genetically modified endothelial cells," Science, 244:1344–1346, 1989.

Winoto and Baltimore, "$\alpha\beta$-lineage-specific Expression of the $\alpha$ T-Cell Receptor Gene by Nearby Silencers," Cell, 59:649, 1989.

Wong et al., "Appearance of $\beta$-lactamase activity in animal cells upon liposome mediated gene transfer," Gene, 10:87–94, 1980.

Wu and Wu, "Receptor-mediated in vitro gene transfections by a soluble DNA carrier system," J. Biol. Chem., 262:4429–4432, 1987.

Wu and Wu, Biochem., 27:887–892, 1988.

Xiao, Li, Samulski, "Efficient long-term gene transfer into muscle tissue of immunocompetent mice by adeno-associated virus vector," J Virol, 70:8098–8108, 1996.

Yeh and Perricaudet, "Advances in adenoviral vectors: from genetic engineering to their biology,: FASEB J, 11:615–623, 1997.

Yutzey, Kline, and Konieczny, "An Internal Regulatory Element Controls Troponin I Gene Expression," Mol. Cell. Biol., 9:1397, 1989.

Zhu, Wu, Liu, Gordon, Anderson, Starnes, Hall, "Down-regulation of cyclin G1 expression by retrovirus-mediated antisense gene transfer inhibits vascular smooth muscle cell proliferation and neointima formation," Circ, 96:628–635, 1997.

Zoldhelyi, McNatt, Shelat, Yamamoto, Chen, Willerson, "Thromboresistance of balloon-injured porcine carotid arteries after local gene trasnfer of human tissue factor pathway inhibitor," Circ, 101:289–295, 2000.

Zoldhelyi, McNatt, Xu, Loose-Mitchell, Meidell, Clubb, Buja, Willerson, Wu, "Prevention of arterial thrombosis by adenoviral-mediated transfer of cyclooxygenase gene," Circ, 93:10–17, 1996.

What is claimed is:

1. A method of expressing a heterologous nucleic acid sequence in a vascular cell in vivo comprising administering to a blood vessel of a mammal a recombinant replicating herpes simplex viral vector at least one expressible $\gamma_1 34.5$ gene and operably comprising a heterologous nucleic acid.

2. The method of claim 1, wherein the recombinant HSV vector lacks two expressible $\gamma_1 34.5$ genes.

3. The method of claim 1, wherein the vascular cell is an endothelial cell.

4. The method of claim 1, wherein the vascular cell is a smooth muscle cell.

5. The method of claim 1, wherein the vascular cell is an adventitial cell.

6. The method of claim 1, wherein the heterologous nucleic acid sequence encodes a polypeptide.

7. The method of claim 6, wherein the polypeptide is selected from the group consisting of an antiproliferative polypeptide, a vasodilatory polypeptide, and an angiogenic polypeptide.

8. The method of claim 1, wherein the heterologous nucleic acid sequence encodes an antisense oligonucleotide or antisense polynucleotide.

9. The method of claim 8, wherein the antisense oligonucleotide or antisense polynucleotide is complementary to an RNA encoding an antiproliferative polypeptide, vasodilatory polypeptide, or angiogenic polypeptide.

10. The method of claim 1, wherein the herpes simplex virus is HSV-1.

11. The method of claim 1, wherein the herpes simplex virus is HSV-2.

12. The method of claim 1, wherein the recombinant replicating herpes simplex virus is administered by a catheter.

13. The method of claim 12, wherein the catheter comprises a balloon.

14. The method of claim 1, wherein the blood vessel is an artery.

15. The method of claim 1, wherein the blood vessel is a vein.

16. The method of claim 1, wherein the blood vessel is the heart.

17. The method of claim 1, wherein the vascular cell is a neointimal cell.

18. The method of claim 1, wherein less than $10^9$ pfu per ml of the vector is administered.

19. The method of claim 18, wherein less than $10^8$ pfu per ml of the vector is administered.

20. The method of claim 1, wherein the heterologous nucleic acid sequence is expressed at least 7 days after the administration of the vector.

21. The method of claim 20, wherein the heterologous nucleic acid sequence is expressed at least 28 days after the administration of the vector.

22. The method of claim 21, wherein the heterologous nucleic acid sequence is expressed at least 70 days after the administration of the vector.

23. The method of claim 1, further comprising the step of administering to the mammal an amount of an antiviral agent effective to attenuate infection by the recombinant replicating herpes simplex viral vector.

24. The method of claim 1, further comprising the step of administering to the mammal an amount of an antiviral agent effective to eliminate infection by the recombinant replicating herpes simplex viral vector.

25. The method of claim 23, wherein the antiviral agent is a nucleoside analog.

26. The method of claim 24, wherein the antiviral agent is a nucleoside analog.

27. The method of claim 25, wherein the nucleoside analog is acyclovir or a pharmaceutically acceptable salt thereof.

28. The method of claim 26, wherein the nucleoside analog is acyclovir or a pharmaceutically acceptable salt thereof.

* * * * *

UNITED STATES PATENT AND TRADEMARK OFFICE
CERTIFICATE OF CORRECTION

PATENT NO. : 6,846,670 B2  Page 1 of 1
APPLICATION NO. : 09/995475
DATED : January 25, 2005
INVENTOR(S) : Lewis B. Schwartz et al.

It is certified that error appears in the above-identified patent and that said Letters Patent is hereby corrected as shown below:

Column 68, line 52, "viral vector at least" should be --viral vector lacking at least--.

Signed and Sealed this

Thirty-first Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 6,846,670 B2 Page 1 of 1
APPLICATION NO. : 09/995475
DATED : January 25, 2005
INVENTOR(S) : Lewis B. Schwartz et al.

It is certified that error appears in the above-identified patent and that said Letters Patent is hereby corrected as shown below:

Col. 1, line 7: Please delete "The United States Government may own certain rights in this invention." Please insert --This invention was made with government support under National Institutes of Health grant number HL007237. The government has certain rights in the invention.--

Signed and Sealed this

Sixth Day of May, 2008

JON W. DUDAS
*Director of the United States Patent and Trademark Office*